(12) United States Patent
Haaring et al.

(10) Patent No.: US 12,364,221 B2
(45) Date of Patent: *Jul. 22, 2025

(54) **GENETIC BASIS FOR *PYTHIUM* RESISTANCE**

(71) Applicant: RIJK ZWAAN ZAADTEELT EN ZAADHANDEL B.V., De Lier (NL)

(72) Inventors: Cornelis Haaring, De Lier (NL); Adrianus Cornelis Koeken, De Lier (NL); Lena Johanna Huijbregts-Doorduin, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/352,428

(22) Filed: Jul. 14, 2023

(65) Prior Publication Data

US 2024/0065191 A1 Feb. 29, 2024

Related U.S. Application Data

(63) Continuation of application No. 18/057,280, filed on Nov. 21, 2022, now abandoned, which is a continuation-in-part of application No. 16/708,680, filed on Dec. 10, 2019, now Pat. No. 11,516,980, which is a continuation-in-part of application No. PCT/EP2018/069649, filed on Jul. 19, 2018.

(30) Foreign Application Priority Data

Jul. 20, 2017 (WO) ................. PCT/EP2017/068398

(51) Int. Cl.
*A01H 1/04* (2006.01)
*A01H 6/34* (2018.01)

(52) U.S. Cl.
CPC ............. *A01H 1/045* (2021.01); *A01H 6/346* (2018.05)

(58) Field of Classification Search
None
See application file for complete search history.

(56) References Cited

U.S. PATENT DOCUMENTS

2023/0189732 A1 6/2023 Liberti et al.

FOREIGN PATENT DOCUMENTS

| WO | 2010/064934 A1 | 6/2010 |
| WO | 2013/001435 A1 | 1/2013 |
| WO | 2013/068958 A1 | 5/2013 |

OTHER PUBLICATIONS

Database Accession No. PREV201500072090: Xu, et al., The Role of Ethylene Response Factors in Cucumber (*Cucumis sativus* L.) Under Waterlogging Stress, Database Biosis (Online) Biosciences Information Service, Philadelphia PA US (2012) & Cucurbitaceae 2012: Proceedings of the Xth EUCARPIA Meeting on Genetics and Breeding of Cucurbitaceae; Antalya, Turkey (2012).
Database Accession No. Q5S004: Subname: Full =Ethylene Response Factor 1 {ECO:000313 | EMBL:AAV66332.1} Dec. 21, 2004.
Siva Sabaratnam, Pythium Diseases on Greenhouse Vegetables, Mar. 2016. Retrieve from the Internet: URL: HTTPS://www.researchgate.net/file.PostFileLoader.html?id=589f0c41615e27bfd26bdce4&assetKey=AS:460563772907523@1486818368887 [retrieved on Sep. 11, 2017].
A.P. Trivilin, et al., Components of Different Signalling Pathways Regulated by a New Orthologue of AtPROPEP1 in Tomato Following Infection by Pathogens, Plant Pathology (2014) vol. 63, p. 1110-1118.
International Search Report and Written Opinion dated Oct. 4, 2018 issued in PCT/EP2018/0696499.
Pan et al., Frontiers in Plant Science (2018) 9: 1-12.
Non-Final Office Action issued Mar. 18, 2025 in U.S. Appl. No. 17/912,364 applying equivalent of present aplpication as anticipation of subject claimed in U.S. Appl. No. 17/912,364 and confirming priority date of claimed subject matter of present application.
Third Part Submission Pursuant to 37 CFR 1.290 submitted on Mar. 7, 2024 in U.S. Appl. No. 17/912,364, published as U.S. 20230189732 (showing U.S. Appl. No. 18/352,428 (present application) and corresponding prior publications thereof are novelty-destroying prior art to subject matter claimed in U.S. Appl. No. 17/912,364).

*Primary Examiner* — Brent T Page
(74) *Attorney, Agent, or Firm* — Duane Morris LLP; Thomas J. Kowalski

(57) ABSTRACT

The present invention relates to a *Cucumis sativus* plant which comprises a copy number variant region which leads to *Pythium* and *Didymella brioniae* resistance. The invention further relates to propagation material suitable for producing such *Cucumis sativus* plant. The invention also relates to a method for producing such *Cucumis sativus* plant and to methods for identification and selection of such a plant. In addition, the invention relates to a marker for identification of the copy number variant region resulting in *Pythium* and *Didymella brioniae* resistance in *Cucumis sativus*, and to use of said marker. The invention also relates to seed which comprises the copy number variant region which leads to *Pythium* and *Didymella brioniae* resistance in the plant grown from such seed.

14 Claims, 5 Drawing Sheets
(2 of 5 Drawing Sheet(s) Filed in Color)
Specification includes a Sequence Listing.

FIG. 1

*Ethylene responsive transcription factor* (ERF) gene sequences

SEQ ID No. 17 – Cucumis sativus
> class=Sequence position=cs_9930_V2_Chr3:9197024..9197710 (- strand)

ATGGATTATT CTGCATTCAT CTCCCCGCTT TCTGATTTCT CATCCGAATC ATCTTTCGGT TCACCCGAAT CCTCCTTCAC
CAATTTGGAC CATAATTTTC TCCCTTTCAA TGAAAATGAC TCAGAGGAAA TGCTTCTTTA CGGCCTAATC
TCCGAGGGCA CATACGAATC ATTCGATACA AGTATCGGAA CCGTGCAAGT GAAGGAAGAG GAAGTCGATT
CCATCGGAGA AGAAAGCCCG AAGAAAGAGA GGGCTTATAG AGGAGTTCGC CGCCGTCCAT GGGGGAAATT
TGCGGCGGAA ATTAGAGATT CCACTAGACA TGGTACAAGG GTATGGTTGG GAACTTTCGA TAGTGCTGAA
GCCGCCGCTT TGGCTTACGA TCAAGCTGCC TTTTCGATGA GGGGCGCTGC CGCAATTCTC AATTTTCCTG
TCGACAGAGT TAGAGAGTCT CTCAAAGAGA TGAACGCCGG CAGTGGGGGC AGCGGTGATA GTTTAGCCGA
AGACGGCGGC TCTCCGGTAG TGGCGTTAAA AGAAAACAC TCGATTAGAA GGAAAGCCAT AGGTAAAAAG
AGCAAAGAGA GAGATGTGAG GATTCAAACT GTGGTGGTTT TGGAAGATTT AGGGACAGAG TATTTGGAAG
AACTTTTGGG GTCTTCTCAA AGTGATAGCC CTTCTTGTTC TTTCTAA

SEQ ID No. 18 – Cucumis sativus
> class=Sequence position= cs_9930_V2_Chr3:9208901..9209353 (+ strand)

ATGGAGGATC ATCGTAAGGG TAAAGAACAA CAAAAGCATG GTGACGATGG GATCAAGTAC CGGGGTGTGC
GACGTCGCCC ATGGGGGAAA TATGCAGCGG AGATACGTGA TCCGTCGAAG AATGGGGCTA GACAATGGCT
TGGGACCTAC GAAACGGCGG AGGATGCAGC TAGGGCTTAC GATCAGAGGG CATTTCAGTT GAAAGGTCAT
CTTGCTAGTT TGAATTTTCC TAGTGAATAT TATGCTCGTG TCATGGGTTC ACCTCCTCAT CCTCCTAACT TGTTTTCTTC
GACTTCGATC AATTCGGGTT TTGACAGCGG TGGTGTTGGT GGTGGATCGT CGACTTCTAA CATCGATCCT
CACAAAGTTA TTGTGTTTGA GTATGTGGAT GGTAGGGTTT TGGAAGACCT TCTGGCTCAA GAGGATAAAA
AGAAGAAGAA GAATAGTAAA TAA

SEQ ID No. 19 – Cucumis sativus
> class=Sequence position= cs_9930_V2_Chr3:9217516..9217917 (- strand)

ATGGACGAGA GTGGTGGTCG TGGAAGAGGT TATGGGGACG ACTCCACAGG CAGCAGAGAG ATTCGTTACC
GGGGAGTACG ACGTCGGCCA TGGGGAAAAT TCGCTGCTGA AATACGAGAC TCTAGAAGGC AAGGAGTACG
GATATGGCTA GGGACTTTCA ACACTGCAGA AGAAGCAGCA CGAGCTTACG ATCGAGCGGC CTACAACATG
AGGGGTCATT TGGCCATTTT GAATTTTCCT AATGAATATC CGCTTACCAG GGTGGGGCT TATTCGAGTG
GGTCATCTTC TTCTTCTTCA ATGTCAATGC GGCAAAATGA AGTGATTGAA TTTGAGTATT TGGATGATAA
AGTGCTGGAA GATCTTCTTG ACTATGGAGA AGAAAGTGAT AAGAGAAGCT AA

FIG. 2

| | | | | Phenotype | | |
|---|---|---|---|---|---|---|
| CNV-het (H) | CNV-hom (R) | Wildtype (S) | | | | |
| AB | BB | AA | SEQ ID No.1 | 8423638 | SEQ ID No.1 | QTL start |
| AB | BB | AA | SEQ ID No.3 | 9082698 | SEQ ID No.3 | |
| AB | BB | AA | SEQ ID No.4 | 9138798 | SEQ ID No.4 | |
| | | | | 9138860 | | CNV-start |
| AAB | AABB | AA | SEQ ID No.6 | 9175772 | SEQ ID No.6 | |
| AAB | AABB | AA | SEQ ID No.7 | 9188302 | SEQ ID No.7 | |
| AAB | AABB | AA | SEQ ID No.8 | 9188499 | SEQ ID No.8 | |
| AAB | AABB | AA | SEQ ID No.9 | 9193352 | SEQ ID No.9 | |
| ABB | BBBB | AA | SEQ ID No.10 | 9195431 | SEQ ID No.10 | |
| ABB | BBBB | AA | SEQ ID No.11 | 9196292 | SEQ ID No.11 | |
| | | | | 9197024 | | ERF1b |
| ABB | BBBB | AA | SEQ ID No.12 | 9201783 | SEQ ID No.12 | |
| | | | | 9208901 | | ERF098 |
| ABB | BBBB | AA | SEQ ID No.13 | 9216644 | SEQ ID No.13 | |
| | | | | 9217917 | | ERF096 |
| AAB | AABB | AA | SEQ ID No.14 | 9257623 | SEQ ID No.14 | |
| AAB | AABB | AA | SEQ ID No.15 | 9273716 | SEQ ID No.15 | |
| AAB | AABB | AA | SEQ ID No.16 | 9279567 | SEQ ID No.16 | |
| | | | | 9286145 | | CNV-end |
| | | | | (copy) | | CNV-start |
| | | | | (copy) | SEQ ID No.6 | |
| | | | | (copy) | SEQ ID No.7 | |
| | | | | (copy) | SEQ ID No.8 | |
| | | | | (copy) | SEQ ID No.9 | |
| | | | | (copy) | SEQ ID No.10 | |
| | | | | (copy) | SEQ ID No.11 | |
| | | | | (copy) | | ERF1b |
| | | | | (copy) | SEQ ID No.12 | |
| | | | | (copy) | | ERF098 |
| | | | | (copy) | SEQ ID No.13 | |
| | | | | (copy) | | ERF096 |
| | | | | (copy) | SEQ ID No.14 | |
| | | | | (copy) | SEQ ID No.15 | |
| | | | | (copy) | SEQ ID No.16 | |
| | | | | (copy) | | CNV-end |
| AB | BB | AA | SEQ ID No.5 | 9294008 | SEQ ID No.5 | |
| AB | BB | AA | SEQ ID No.2 | 10261179 | SEQ ID No.2 | QTL end |

Score A — Score B ---

FIG. 3

**AP-2 domain sequences of the *ERF* genes in the CNV**

SEQ ID No. 20 – AP-2 domain of the *ERF* gene represented by SEQ ID No. 17

YRGVRRRPWGKFAAEIRDSTRHGTRVWLGTFDSAEAAALAYDQAAFSMRGAAAILNFPVD

SEQ ID No. 21 – AP-2 domain of the *ERF* gene represented by SEQ ID No. 18

YRGVRRRPWGKYAAEIRDPSKNGARQWLGTYETAEDAARAYDQRAFQLKGHLASLNFPSE

SEQ ID No. 22 – AP-2 domain of the *ERF* gene represented by SEQ ID No. 19

YRGVRRRPWGKFAAEIRDSRRQGVRIWLGTFNTAEEAARAYDRAAYNMRGHLAILNFPNE

FIG. 4

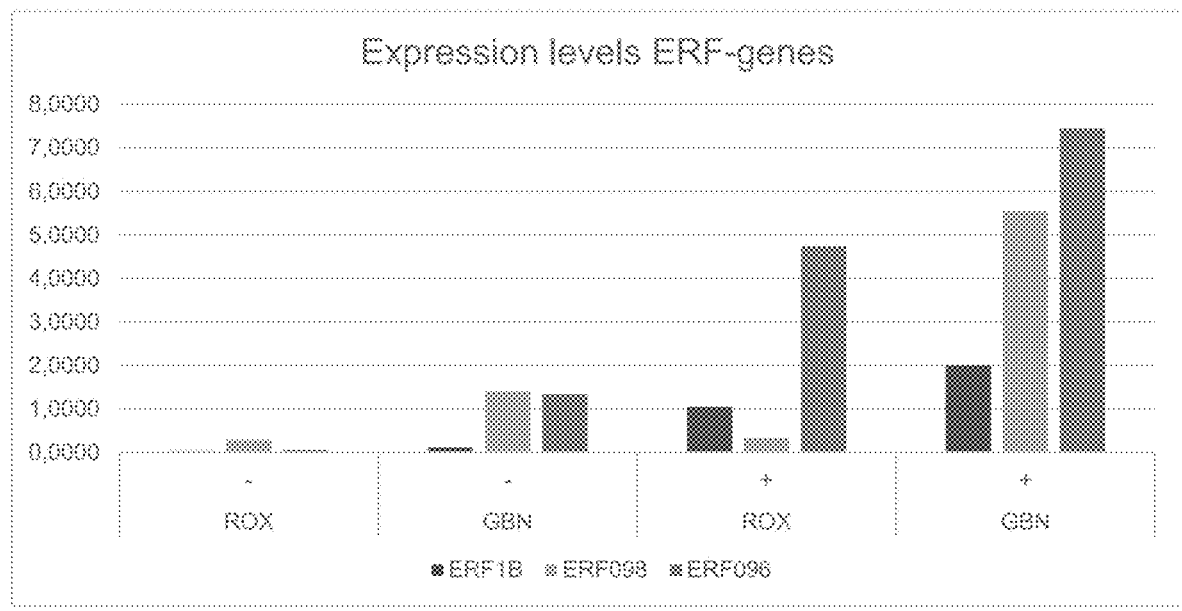

US 12,364,221 B2

SEQUENCE LISTING

```
Sequence total quantity: 22
SEQ ID NO: 1              moltype = DNA  length = 201
FEATURE                   Location/Qualifiers
source                    1..201
                          mol_type = other DNA
                          organism = Cucumis sativus
SEQUENCE: 1
tggctcctga tcgtggtgcc acagtcccaa aatttggtga ctgggacgaa agcgatccat  60
cgtcatctga gaactgcact aatattttca ccagagtgcg tgtggagaga caaacggaag 120
acggaagttt gccagctggg accaatgttt ctagtattcg tagtcgttct agtgccgaaa 180
actcaaagag atgttgctgt t                                          201

SEQ ID NO: 2              moltype = DNA  length = 201
FEATURE                   Location/Qualifiers
source                    1..201
                          mol_type = other DNA
                          organism = Cucumis sativus
SEQUENCE: 2
attaaactt atgaaggttt cccttttat ctttccttta tccaacaaat aaattcttat  60
ttacaactcc acaaacttaa ttatatccca atttggtatc tttcaatctt cttcctctta 120
```

```
aacagcaact tgggctgcag ccaatcttgc taccggaact ctgaaaggag aacaagaaac    180
atagtcaagt ccagcctcag c                                             201

SEQ ID NO: 3           moltype = DNA   length = 201
FEATURE                Location/Qualifiers
source                 1..201
                       mol_type = other DNA
                       organism = Cucumis sativus
SEQUENCE: 3
taataaaaca ttatatatat atttrcatca aatatatata aattaaaaaa aattaaaatag    60
actcgtaaga aaggtgtaaa tcaaataaca aaaaaatttt gaaataaatt taactcactt   120
cttatcttat tcaattatttt tatcttgcat gaaattttgt taagaataat agtttktata   180
tttagagatc krttaakatt t                                              201

SEQ ID NO: 4           moltype = DNA   length = 400
FEATURE                Location/Qualifiers
source                 1..400
                       mol_type = other DNA
                       organism = Cucumis sativus
SEQUENCE: 4
gatacgaaac tgtctttaat tatttaaact tgagtgtgga tcaaaacac atttacaata     60
gtcgttaaag attagagaaa gcttggattt taggaattaa agatttcaaa ccattatttg   120
gtcactttgg taggattgca agcttcaaga ggacttgaca gatgaaatgg ttggtttagc   180
aaagcagtcg aagagagcag tctgataacg agccaatcct tagagagcat tgagaaagta   240
tattttctct actaatcgtt cattgctgac gtagtagata tagaaatttt atacctttgg   300
tttcttcaaa atataaacaa acgctataga aattaaaata ggaaagtctt cgattcgtcc   360
catattcaaa gcatagtttg agcaattctg ttttcagtg                         400

SEQ ID NO: 5           moltype = DNA   length = 201
FEATURE                Location/Qualifiers
source                 1..201
                       mol_type = other DNA
                       organism = Cucumis sativus
SEQUENCE: 5
atttaatct aatagagagt gattaactca tgctaggcac attttaataa tcatattaac     60
tgcattctaa tttaacaatg taaaatgact tttattatac ctatttggag aattttgtta   120
ttttattatt attgttttttt tttactacac aatttttcatt taaataacca gaaaaatgat   180
tgacttccac tattttaaaa a                                             201

SEQ ID NO: 6           moltype = DNA   length = 193
FEATURE                Location/Qualifiers
source                 1..193
                       mol_type = other DNA
                       organism = Cucumis sativus
variation              111..121
                       note = a, c, t, or g
SEQUENCE: 6
aaatatttcc atatacgtgt aggcaatggt ggtaaatacc tagaggcgtc aagatccaat     60
cataggagca cagcgatctc aactatttg tggttgcrcc ggaaaatggg nnnnnnnnnn    120
ntgaggatga ggaagaggag agggagggc tatggagaga aatggggag gaggtgatgg     180
ggatatttaa gaa                                                      193

SEQ ID NO: 7           moltype = DNA   length = 195
FEATURE                Location/Qualifiers
source                 1..195
                       mol_type = other DNA
                       organism = Cucumis sativus
SEQUENCE: 7
atatcagaag aaaaaaaata gactgaatta atcatggatt ttgaaaaact tttttttttt     60
tcaagtaata tattcttaag aaacctttag aatccatttt gcataaaatg acattctttt   120
ttatttacat ttggaaaaat accatttttt tattcaaatg aaaattatga aaatagcta    180
aataaataaa atatt                                                    195

SEQ ID NO: 8           moltype = DNA   length = 100
FEATURE                Location/Qualifiers
source                 1..100
                       mol_type = other DNA
                       organism = Cucumis sativus
variation              44
                       note = a, c, t, or g
SEQUENCE: 8
gtcctttata aaaatttga aacgtaaata gttggatttt tctnaaaaaa aaatagaga      60
ctatgtgtca tttatatcat gtcaataaga tggtctagaa                        100

SEQ ID NO: 9           moltype = DNA   length = 195
FEATURE                Location/Qualifiers
source                 1..195
                       mol_type = other DNA
                       organism = Cucumis sativus
```

| variation | 98 |
| --- | --- |
| | note = a, c, t, or g |

SEQUENCE: 9

```
aagcaaccta ttaattattc tattgagggt agcagattcc atcttagagt tcctgcttca    60
atccaagtga aaaagaaaa aagaaaaaag aaaawaanat cattcagatc aaacaaaata   120
gcagtagtaa agtaaaaaga aaaaaaaaaa aaaaaaagca gaataaaggc agcaacgtac   180
ttggatgttg agggg                                                    195
```

| SEQ ID NO: 10 | moltype = DNA   length = 181 |
| --- | --- |
| FEATURE | Location/Qualifiers |
| source | 1..181 |
| | mol_type = other DNA |
| | organism = Cucumis sativus |
| variation | 1 |
| | note = a, c, t, or g |

SEQUENCE: 10

```
nacacacaca cacacattat caagcaaaac atcactaatt ccaaatgata attgtgtaac    60
attaattgaa aattccacat gaaaaaactg aaagaatgaa ttgacatcac actctattat   120
aatatatatg aactgctttc ttaattctca attagttttg agataaaaat aaatatatta   180
a                                                                   181
```

| SEQ ID NO: 11 | moltype = DNA   length = 199 |
| --- | --- |
| FEATURE | Location/Qualifiers |
| source | 1..199 |
| | mol_type = other DNA |
| | organism = Cucumis sativus |
| variation | 31 |
| | note = a, c, t, or g |
| variation | 151..166 |
| | note = a, c, t, or g |

SEQUENCE: 11

```
tattattgga aatgattttg attttgaata naaaaaggt gagatccatg ttatgtatac    60
attacaatca aatgataaay aatgaattaa tgtgtggaat gatgcaatct aaaatttgg   120
acatgcacaa aatagaaaac atcatgcatc nnnnnnnnnn nnnnnntaca tatactttta   180
gaacaacctt ccatcaaat                                                199
```

| SEQ ID NO: 12 | moltype = DNA   length = 201 |
| --- | --- |
| FEATURE | Location/Qualifiers |
| source | 1..201 |
| | mol_type = other DNA |
| | organism = Cucumis sativus |

SEQUENCE: 12

```
taaaaaatgt tagataacaa atgacagcta gaaaataaat tagtatttta tcttatatga    60
gttttttttt tttttttaaa aatatcttct tctaagaaat gaaattatttt tccttttttag  120
aaatttctaa aatttaggaa atcaaattat tctcccttttt caaatcttta aaattttagga  180
cgtaaataat ttgatatttg g                                             201
```

| SEQ ID NO: 13 | moltype = DNA   length = 190 |
| --- | --- |
| FEATURE | Location/Qualifiers |
| source | 1..190 |
| | mol_type = other DNA |
| | organism = Cucumis sativus |

SEQUENCE: 13

```
ttatgtaaaa tatcaaatac aaaagtgaaa atatagaaat tattcgtgtg ataacttact    60
aatttcaata catttaaggt taaaatttta attattattt caagaagta ttgtttacct   120
caaggaagaa tcttacatga atcaataatc attggtctta tgattaatct tttttttcttt  180
cgaaacattt                                                          190
```

| SEQ ID NO: 14 | moltype = DNA   length = 201 |
| --- | --- |
| FEATURE | Location/Qualifiers |
| source | 1..201 |
| | mol_type = other DNA |
| | organism = Cucumis sativus |

SEQUENCE: 14

```
gggcactgat atagccaaag ctatccctcc aattggtrat ggctgcagag tacagatcga    60
aattactatt gtaaatcaaa ggtttggtga ggtcgcgagt ttaatattgt ttcttggatt   120
cggtttcttg ctcgtgaaat cttcgaactg catctttcat ctcctcaaga acgttctccg   180
gaatcccatg gttaatcagt t                                             201
```

| SEQ ID NO: 15 | moltype = DNA   length = 201 |
| --- | --- |
| FEATURE | Location/Qualifiers |
| source | 1..201 |
| | mol_type = other DNA |
| | organism = Cucumis sativus |

SEQUENCE: 15

```
tcacaatgaa ttctttttttt atttgaaraa catctattag aaagactgtt tatcatgatc    60
ccttcccttc aggtaccacc catgggttta ttcttcccaa cgcttttggt tccagatgtg   120
tatccaccac caccccgtgc atggtcagtt gctaataatc atattcaact agttttcatg   180
tcaaaatata cctgtatgat g                                             201
```

```
SEQ ID NO: 16           moltype = DNA  length = 201
FEATURE                 Location/Qualifiers
source                  1..201
                        mol_type = other DNA
                        organism = Cucumis sativus
SEQUENCE: 16
taaamagagc cataaagtaa tcaggtagag ttaaacccag atccaactcc cgcatgtaca    60
ggaccccccg atcgctcctc atgatcaaat agtcatggct gagtgccaat gtaaagccag   120
cggcagcagc gtgtcctgta atggcagcaa tggtaggcat aggaagggaa atgarttcgg   180
caacgacgga cttgaagatc t                                             201

SEQ ID NO: 17           moltype = DNA  length = 687
FEATURE                 Location/Qualifiers
misc_feature            1..687
                        note = ERF
source                  1..687
                        mol_type = other DNA
                        organism = Cucumis sativus
SEQUENCE: 17
atggattatt ctgcattcat ctccccgctt tctgatttct catccgaatc atctttcggt    60
tcacccgaat cctccttcac caatttggac cataattttc tccctttcaa tgaaaatgac   120
tcagaggaaa tgcttcttta cggcctaatc tccgagggca catacgaatc attcgataca   180
agtatcggaa ccgtgcaagt gaaggaagag aagtcgatt ccatcggaga agaaagcccg    240
aagaaagaga gggcttatag aggagttcgc cgccgtccat gggggaaatt tgcggcggaa   300
attagagatt ccactagaca tggtacaagg gtatggttgg gaacttttcga tagtgctgaa   360
gccgccgctt tggcttacga tcaagctgcc ttttcgatga ggggcgctgc cgcaattctc   420
aattttcctg tcgacagagt tagagagtct ctcaaagaga tgaacgccgg cagtgggggc   480
agcggtgata gtttagccga agacggcggc tctccggtag tggcgttaaa aagaaaacac   540
tcgattagaa ggaaagccat aggtaaaaag agcaaagaga gagatgtgag gattcaaact   600
gtggtggttt tggaagattt agggacagag tatttggaag aacttttggg gtcttctcaa   660
agtgatagcc cttcttgttc tttctaa                                       687

SEQ ID NO: 18           moltype = DNA  length = 453
FEATURE                 Location/Qualifiers
misc_feature            1..453
                        note = ERF
source                  1..453
                        mol_type = other DNA
                        organism = Cucumis sativus
SEQUENCE: 18
atggaggatc atcgtaaggg taagaacaa caaaagcatg gtgacgatgg gatcaagtac     60
cggggtgtgc gacgtcgccc atgggggaaa tatgcagcgg agatacgtga tccgtcgaag   120
aatggggcta gacaatggct tgggacctac gaaacggcgg aggatgcagc tagggcttac   180
gatcagaggg catttcagtt gaaaggtcat cttgctagtt tgaattttcc tagtgaatat   240
tatgctcgtg tcatgggttc acctcctcat cctcctaact tgttttcttc gacttcgatc   300
aattcgggtt ttgacagcgg tggtgttggt ggtggatcgt cgacttctaa catcgatcct   360
cacaaagtta ttgtgtttga gtatgtggat ggtaggggtt tggaagacct tctggctcaa   420
gaggataaaa agaagaagaa gaatagtaaa taa                                453

SEQ ID NO: 19           moltype = DNA  length = 402
FEATURE                 Location/Qualifiers
misc_feature            1..402
                        note = ERF
source                  1..402
                        mol_type = other DNA
                        organism = Cucumis sativus
SEQUENCE: 19
atggacgaga gtggtggtcg tggaagaggt tatggggacg actccacagg cagcagagag    60
attcgttacc ggggagtacg acgtcggcca tggggaaaat cgctgctga aatacgagac    120
tctagaaggc aaggagtacg gatatggcta gggactttca acactgcaga gaagcagca   180
cgagcttacg atcgagcggc ctacaacatg aggggtcatt tggccatttt gaattttcct   240
aatgaatatc cgcttaccag gggtgggggct tattcgagtg ggtcatcttc ttcttcttca   300
atgtcaatgc ggcaaaatga agtgattgaa tttgagtatt tggatgataa agtgctggaa   360
gatcttcttg actatggaga agaaagtgat aagagaagct aa                      402

SEQ ID NO: 20           moltype = AA  length = 60
FEATURE                 Location/Qualifiers
REGION                  1..60
                        note = AP-2 domain of SEQ ID No. 17
source                  1..60
                        mol_type = protein
                        organism = Cucumis sativus
SEQUENCE: 20
YRGVRRRPWG KFAAEIRDST RHGTRVWLGT FDSAEAAALA YDQAAFSMRG AAAILNFPVD    60

SEQ ID NO: 21           moltype = AA  length = 60
FEATURE                 Location/Qualifiers
REGION                  1..60
```

-continued

```
                    note = AP-2 domain of SEQ ID No. 18
source              1..60
                    mol_type = protein
                    organism = Cucumis sativus
SEQUENCE: 21
YRGVRRRPWG KYAAEIRDPS KNGARQWLGT YETAEDAARA YDQRAFQLKG HLASLNFPSE  60

SEQ ID NO: 22       moltype = AA  length = 60
FEATURE             Location/Qualifiers
REGION              1..60
                    note = AP-2 domain of SEQ ID No. 19
source              1..60
                    mol_type = protein
                    organism = Cucumis sativus
SEQUENCE: 22
YRGVRRRPWG KFAAEIRDSR RQGVRIWLGT FNTAEEAARA YDRAAYNMRG HLAILNFPNE  60
```

GENETIC BASIS FOR *PYTHIUM* RESISTANCE

RELATED APPLICATIONS AND INCORPORATION BY REFERENCE

This application is a continuation of U.S. patent application Ser. No. 18/057,280 filed Nov. 21, 2022, which is a continuation-in-part application of U.S. patent application Ser. No. 16/708,680 filed Dec. 10, 2019, now U.S. Pat. No. 11,516,980, which is a continuation-in-part application of international patent application Serial No. PCT/EP2018/069649 filed 19 Jul. 2018, which published as PCT Publication No. WO 2019/016323 on 24 Jan. 2019, which claims benefit of international patent application Serial No. PCT/EP2017/068398 filed 20 Jul. 2017.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE STATEMENT

The instant application contains a Sequence Listing which has been submitted electronically and is hereby incorporated by reference in its entirety. Said ASCII copy, is named Y7954-01449.xml and is 29,372 bytes in size.

FIELD OF THE INVENTION

The present invention relates to a *Pythium* and *Didymella brioniae* resistant *Cucumis sativus* plant which comprises a copy number variant region leading to the resistances. The invention further relates to a method for producing such *Cucumis sativus* plant and methods for identification and selection of such a plant. The invention also relates to progeny, seed and fruit of the *Pythium* and *Didymella brioniae* resistant *Cucumis sativus* plant, to propagation material suitable for producing the *Cucumis sativus* plant, and to a food product which comprises such cucumber fruit or part thereof. The invention also relates to a marker for identification of the copy number variant region resulting in *Pythium* and *Didymella brioniae* resistance in *Cucumis sativus*, and to use of said marker.

BACKGROUND OF THE INVENTION

In many crops, the raising of seedlings or the initial growth stage of a plant is hampered by a phenomenon known as 'damping off'. Damping off is a soil-borne problem that can be caused by a number of pathogens. The most common of these pathogens are various *Pythium, Phytophthora, Rhizoctonia*, and *Fusarium* species. Damping off is also known as root rot, since the symptoms are usually visible as rotting of the stem and root tissues above or below the soil surface. Damping off can occur pre-emergence, whereby it can initially be confused with a poor seed viability. Often, however, the tissue of just germinated plants becomes water-soaked near the soil surface, after which the seedlings topple over and die.

Very often the cause of damping off turns out to be one of a rather large number of *Pythium* species. *Pythium*, like *Phytophthora*, is a genus of the *Oomycetes*; the *Pythium* species are usually very generalistic and have a large number of hosts. The differences between the various *Pythium* species lie therefore not in their host-range, but in the different environmental conditions under which they can optimally affect the plants. Although *Pythium* is mostly infecting seedlings, it is also possible that older plants are affected. Because of their non-host specificity, a cultivation method such as crop rotation is not very effective in controlling the disease. In addition, *Pythium* can easily survive in soil and on plant debris for several years, making it difficult to eradicate the pathogen.

Genetic resistance against *Pythium* is not known, and *Pythium* is therefore one of the diseases against which biochemical control is extensively used. *Pythium* can occur in many different environments, also depending on the species; it is often found in protected cultivation, and can be present in soil as well as in various substrates that are used in high-end cultivation systems. Generally wet soil, large temperature changes, and high levels of fertilizer favor the development of the disease. Various fungicides and biological control agents can be used to prevent the occurrence or the spread of the disease. Once plants are infected, treatment to cure them is not effective. Application can be done for example as a seed treatment, soil drenching, or foliar spray. Most effective however is to maintain a strict hygiene system and high level crop maintenance in order to prevent the pathogen from entering the growing system.

Another potentially devastating disease, that in particular affects Cucurbitaceae such as cucumber, melon, and watermelon, is 'gummy stem blight', caused by the pathogen *Didymella brioniae*. The pathogen affects the stem and leaves of the plant, but can also be very harmful to the fruits, where it causes *Didymella* fruit rot, also called black rot, or *Didymella* fruit rot. Resistance to *Didymella brioniae* fruit rot is described in WO2021185774.

Citation or identification of any document in this application is not an admission that such document is available as prior art to the present invention.

SUMMARY OF THE INVENTION

It is an object of the present invention to provide a *Cucumis sativus* plant that is resistant to *Pythium* and *Didymella brioniae* internal fruit rot.

The present invention relates to a copy number variant region (CNV) that is present on chromosome 3 between SEQ ID NO: 4 and SEQ ID NO: 5 of the *C. sativus* genome. This CNV leads to resistance against *Pythium* and internal fruit rot caused by *Didymella brioniae* when present in a cucumber plant, and is further referred to herein as the "copy number variant region of the invention" or the "CNV of the invention". The "CNV of the invention" also encompasses that the presence of this CNV can be identified by at least one of the markers selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The "CNV of the invention" further encompasses that this CNV comprises and therefore is linked to at least one of the markers selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

The present invention provides a *C. sativus* plant which comprises the copy number variant region of the invention.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSIT

Seed of cucumber *Cucumis sativus* EX 5.014 was deposited with NCIMB Ltd, Ferguson Building, Craibstone Estate, Bucksburn, Aberdeen AB21 9YA, UK on Jul. 11, 2017 under deposit accession number NCIMB 42776. The seed of the deposit comprises the QTL, the copy number variant region, and at least two copies of an ERF gene of the invention homozygously. Plants grown from this seed are thus resistant against *Pythium* and against internal fruit rot caused by *Didymella brioniae*.

The Deposits with NCIMB Ltd, under deposit accession number NCIMB 42776 were made and accepted pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 1 depicts genomic coding sequences of SEQ ID NO: 17, SEQ ID NO: 18, and SEQ ID NO: 19.

FIG. 2 depicts representation of the presence of the markers, the location of the ERF genes including the start position of the gene, and the difference between the score of a heterozygous CNV marker and a homozygous CNV marker. CNV-hom shows the marker scores when the QTL or CNV region is homozygously present in a plant. CNV-het shows the marker score when the QTL or CNV region is heterozygously present in a plant.

FIG. 3 depicts sequences of the AP-2 domains SEQ ID NO: 20, SEQ ID NO: 21, and SEQ ID NO: 22 of the 3 ERF genes that are present in the CNV region.

FIG. 4 depicts relative expression of ERF genes that are present in the CNV region of a plant of the invention. ERF1B is the gene represented by SEQ ID NO: 17; ERF098 is the gene represented by SEQ ID No 18; ERF096 is the gene represented by SEQ ID NO: 19.

FIG. 5B shows the entering of the fruit rot at the blossom end scar of the fruit.

DETAILED DESCRIPTION OF THE INVENTION

Figure 5A:
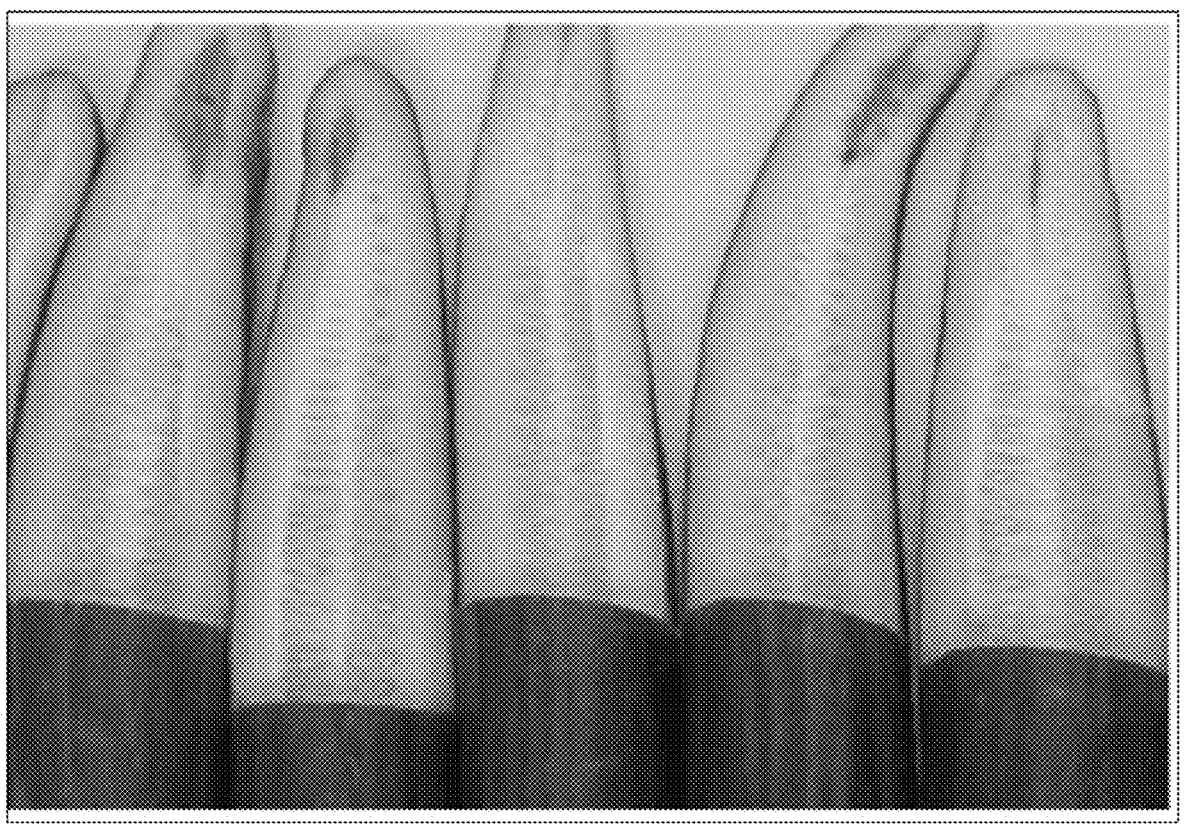
FIGS. 5A and 5B depict *Didymella* internal fruit rot symptoms in cucumber.

Cucumber and gherkin, both belonging to the species *Cucumis sativus*, are among the crops that can be severely affected by various *Pythium* species, among which *Pythium aphanidermatum*, *Pythium dissotocum*, and *Pythium ultimum*. Since no varieties exist that are resistant to *Pythium*, a research program was started to develop *C. sativus* plants that are resistant to this pathogen.

The research program identified a population of plants that showed a remarkably good resistance to *Pythium*. This population of plants, however, had many agronomic characteristics such as pronounced dark warts and spines that needed to be overcome before it could be used in a breeding program to develop commercially suitable *Pythium* resistant cucumber varieties. A lot of effort had to be put in, whereby the plants were combined with various internal breeding lines to develop cucumber material with different backgrounds that could be further used in different combinations for the development of *C. sativus* varieties of different types.

To confirm the resistance and to follow the resistance in populations during the breeding process a bio-assay for *Pythium* resistance was regularly carried out on relevant material (Example 1). However, because bio-assays are commonly time consuming, and logistically challenging since for example a suitable area, sufficient inoculum, and good timing of the evaluation is required, it is more efficient to develop a marker screen. For this purpose a QTL mapping study was performed and a QTL region was identified on chromosome 3 between SEQ ID NO: 1 and SEQ ID NO: 2 (Example 2). A marker within this region that is linked to the QTL is represented by SEQ ID NO: 3. The presence of the QTL that leads to *Pythium* resistance can be identified by one or both of SEQ ID NO: 1 and SEQ ID NO: 3; SEQ ID NO: 1 and SEQ ID NO: 3 are linked to the resistance; SEQ ID NO: 1 and SEQ ID NO: 2 indicate the position of the QTL.

Through further research it was determined that when a certain region of approximately 30 genes in the QTL on chromosome 3 is present in duplicate in a *C. sativus* plant, this duplication leads to resistance against *Pythium* (Example 3). When a duplication, or other multiplication, of a gene or a region of genes is present on a chromosome in a genome, this is called a copy number variant. The presence of multiple copies of a certain gene can lead to an increased expression of said gene, and/or an increase of the product produced by said gene. This increase can subsequently lead to resistance. In the present invention, the duplication of the genes, i.e. a copy number variant, present in the region between SEQ ID NO: 4 and SEQ ID NO: 5 was determined to be related to resistance to *Pythium*.

Additional analysis of the *C. sativus* plants having this copy number variant region was done for internal fruit rot caused by *Didymella brioniae* (Example 5). The bio-assay showed that the presence of the same copy number variant region that leads to *Pythium* resistance, also leads to increased internal fruit rot resistance caused by *Didymella briniae*. Both resistances were therefore present in the deposited seed of NCIMB 42776, which comprise the copy number variant region described herein.

The present invention relates to a copy number variant region (CNV) that is present on chromosome 3 between SEQ ID NO: 4 and SEQ ID NO: 5 of the *C. sativus* genome. This CNV leads to resistance against *Pythium* and to internal fruit rot resistance cause by *Didymella* brionae when present in a cucumber plant, and is further referred to herein as the "copy number variant region of the invention" or the "CNV of the invention". The "CNV of the invention" also encompasses that the presence of this CNV can be identified by at least one of the markers selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The "CNV of the invention" further encompasses that this CNV comprises and therefore is linked to at least one of the markers selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment the copy number variant region of the invention comprises at least two of the markers selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

In one embodiment the copy number variant region of the invention comprises at least two of the markers selected from the group consisting of SEQ ID NO: 11, SEQ ID NO: 12, SEQ ID NO: 13, SEQ ID NO: 14, SEQ ID NO: 15, and SEQ ID NO: 16.

In one embodiment the copy number variant region of the invention comprises at least the markers SEQ ID NO: 13, SEQ ID NO: 14, and SEQ ID NO: 15.

The present invention provides a *C. sativus* plant which comprises the copy number variant region of the invention.

It was further determined that the sequences of the two copies of the duplicated region on chromosome 3 were not identical. Several SNPs were identified which are either present in both copies or only in one of the two copies. The SNPs present in only one of the two copies of the CNV region can be identified by using a polymorphic marker. Examples of markers that are polymorphic between the CNV copies are represented by SEQ ID NO: 6, SEQ ID NO: 7, SEQ ID NO: 8, SEQ ID NO: 9, SEQ ID NO: 14, SEQ ID NO: 15, and SEQ ID NO: 16. These markers are indicated herein as 'heterozygous CNV markers'.

The SNPs present in both copies can be identified by using markers that are polymorphic between both copies of the CNV region on the one hand and only a single, wildtype, copy on the other hand. Examples of markers that are polymorphic between both copies of the CNV region on the one hand and only a single, wildtype, copy on the other hand are represented by SEQ ID NO: 10, SEQ ID NO: 11, SEQ ID NO: 12, and SEQ ID NO: 13. These markers are indicated herein as 'homozygous CNV markers'.

Table 2 shows the marker score for the presence of one copy, and the marker score to identify the presence of the copy number variant region and therefore a resistant plant. When the sequences of the markers are positioned on version 2 of the publicly available genome reference sequence for *C. sativus*, that is based on Cs9930, the physical position to which the SNP polymorphism in said marker sequence corresponds is also indicated in Table 2. The public *C. sativus* genome reference sequence based on Cs9930 can for example be accessed at: http://www.icugi.org/cgi-bin/gb2/gbrowse/cucumber_v2/, and is the reference for 'the public cucumber genome' as used herein. The positions of the QTL or CNV region and the markers of the invention are therefore also derivable from this public map and these positions are relative to said physical positions.

As used herein a marker is genetically "linked", and can be used for the identification of the CNV region of the invention, when the sequence of said marker is present in the CNV of the invention.

FIG. 2 shows the location of the various markers within the QTL and the CNV region, and a representation of the difference in scoring between the so-called heterozygous and homozygous CNV markers.

Within the CNV region of the invention three ERF genes are present. An ERF gene within the CNV region can be identified by the presence of an AP-2 domain. The AP-2 domain is a conserved DNA-binding domain found in transcription regulators in plants, and the skilled person is aware of how to identify the presence of an AP-2 domain in a gene. An AP-2 domain can for example be identified by using the EMBL-EBI database through http://pfam.xfam.org/family/AP2. A search for the relevant sequences can subsequently be performed with for example the use of the hmmsearch from HMMER 3.1b2, using an e-value of 1e-4.

The present invention relates to an ERF gene of which at least two copies are present within the CNV of the invention, on chromosome 3 between SEQ ID NO: 4 and SEQ ID NO: 5 of the *C. sativus* genome. The presence of at least two copies of said ERF gene leads to resistance against *Pythium* when present in a cucumber plant, and is further referred to herein as the "at least two copies of an ERF gene of the invention". The "at least two copies of an ERF gene of the invention" encompasses that the presence of said at least two copies of an ERF gene can be identified by at least one of the markers selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16. The "ERF gene of the invention" encompasses an ERF gene that can be identified by determining the presence of an AP-2 domain represented by SEQ ID NO: 20 or SEQ ID NO: 21 or SEQ ID NO: 22, or by a sequence having a sequence identity of at least 70% to any of those sequences. In order of increased preference, the AP-2 domain sequence of an ERF gene of the invention has a sequence identity of 75%, 80%, 85%, 90%, 93%, 95%, 96%, 97%, 98%, 99%, or 100% to any of the sequences represented by SEQ ID NO: 20 or SEQ ID NO: 21 or SEQ ID NO: 22 (FIG. 3). The "ERF gene of the invention" also encompasses an ERF gene which may comprise a coding sequence represented by SEQ ID NO: 17 or by a sequence having at least 95% sequence identity thereto, designated herein as an ERF1B gene; an ERF gene which may comprise a coding sequence represented by SEQ ID NO: 18 or by a sequence having at least 95% sequence identity thereto, designated herein as an ERF098 gene; or an ERF gene which may comprise a coding sequence represented by SEQ ID NO: 19 or by a sequence having at least 95% sequence identity thereto, designated herein as an ERF096 gene. Preferably, the presence of the at least two copies of an ERF gene of the invention leads to increased expression of said ERF gene.

The present invention also provides a mutant ERF gene of the invention, the presence of which mutant ERF gene leads to Pythium resistance when present in a C. sativus plant. The mutant ERF gene has a higher expression than the wild-type ERF gene, and is further referred to herein as the "mutant ERF gene of the invention". A "mutant ERF gene of the invention" encompasses an ERF gene of the invention having a mutation in the promoter region, a mutation in the 5'-UTR, a mutation in the coding sequence, and/or a mutation in the 3'UTR.

As used herein, the percentage 'sequence identity' is the percentage of nucleotides or amino acids that is identical between two sequences after proper alignment of those sequences. The person skilled in the art is aware of how to align sequences. To obtain the most significant result, the best possible alignment that gives the highest sequence identity score should be obtained. The sequences are compared over the length of the shortest sequence in the assessment.

Increased expression is expression as compared to a plant which may comprise a single, wild-type, copy of the ERF gene, which plant is not resistant to Pythium. Increased expression is optionally determined in the presence of Pythium infection. An increased expression is an at least 1.5 fold increased expression, in order of increased preference an at least 1.9 fold, 2 fold, 2.5 fold, 2.8 fold, 3 fold, 3.5 fold, 4 fold, 4.5 fold, 4.8 fold, 5 fold, 7 fold, 9 fold, 10 fold, 12 fold, 15 fold, 16 fold, 18 fold, 20 fold, 22 fold, 22.9 fold, 25 fold, 30 fold, 35 fold, or higher, up to an at least 100 fold increased expression.

The present invention provides a plant that is resistant to Pythium, which plant may comprise at least two copies of an ERF gene of the invention, or may comprise a mutant ERF gene of the invention.

A plant of the invention preferably may comprise two copies of an ERF gene which may comprise a coding sequence represented by SEQ ID NO: 17 or by a sequence having at least 95% sequence identity thereto, designated herein as an ERF1B gene, two copies of an ERF gene which may comprise a coding sequence represented by SEQ ID NO: 18 or by a sequence having at least 95% sequence identity thereto, designated herein as an ERF098 gene, and two copies of an ERF gene which may comprise a coding sequence represented by SEQ ID NO: 19 or by a sequence having at least 95% sequence identity thereto, designated herein as an ERF096 gene.

As used herein, a copy of an ERF gene is a gene which may comprise at least 95% sequence identity, preferably in order of increased preference at least 96%, 97%, 98%, 99%, or 100% sequence identity, to another gene that is present in the CNV of the invention.

As used herein, a gene may comprise the promoter, the 5'-UTR, the coding sequence (CDS) or gDNA sequence, and the 3'UTR of that gene. The promoter suitably may comprise a sequence of up to 2 kb upstream of the ATG start codon of the CDS of that gene.

The present invention provides a C. sativus plant that is resistant to Pythium, which C. sativus plant may comprise at least two copies of at least one ERF gene of the invention, or may comprise a mutant ERF gene of the invention, wherein the presence of the at least two copies or the mutant ERF gene of the invention leads to increased expression of said ERF gene as compared to a C. sativus plant which may comprise a single, wild-type, copy of said ERF gene.

As used herein, Pythium resistance is resistance to one or more Pythium species, in particular to one or more of the species of the group which may comprise Pythium aphanidermatum, Pythium dissotocum, and Pythium ultimum. As used herein, Pythium resistance comprises resistance to at least the species Pythium aphanidermatum.

The Pythium resistance of the present invention inherits in a monogenic, incompletely dominant, manner. As used herein, incompletely dominant means that when the copy number variant region, the at least two copies of an ERF gene, or the mutant ERF gene of the invention is homozygously present, it gives a higher level of Pythium resistance than when the QTL, the copy number variant region, the at least two copies of an ERF gene, the mutant ERF gene of the invention is heterozygously present. The heterozygous presence of the QTL, the copy number variant region, the at least two copies of an ERF gene, or the mutant ERF gene of the invention however still confers improved Pythium resistance. The improved Pythium resistance of both homozygous and heterozygous plants makes the plants more suitable for cultivation under conditions where Pythium is present. Therefore both levels of resistance are considered to be improved agronomic characteristics.

The presence of Pythium resistance can be determined through a bioassay under conditions that are suitable for Pythium infection. For example the cucumber seedling bioassay as described in Chen et al, 1987 can be used. (Factors affecting suppression of Pythium damping-off in container media amended with composts. Chen et al, Phytopathology 77:755-760, 1987). As container medium a suitable growth medium for the plants to be tested can be used. Regular potting soil is an example of a container medium that can be used in a Pythium bioassay for cucumber.

As used herein, Pythium resistance is determined by comparison to a control variety known to be Pythium susceptible. Resistance is suitably scored on 10-12 plants of a certain line or other plant population to be tested. The use of replicates is advisable, especially when conditions cannot be optimally controlled. Since Pythium shows very severe symptoms, and no adequate cure is possible once a plant has been affected, scoring can be done in just two categories: either resistant or dead/wilted. Scoring is suitably done 1014 days after inoculation. A genotype is considered to be resistant when in a bioassay significantly more plants score resistant than the susceptible control variety in that same bioassay. Depending on the number of plants that is used in the assay, statistical methods known to the skilled person can optionally be used to determine a significant difference.

Figure 5B:

As used herein, Didymella brioniae resistance is resistance to internal fruit rot caused by Didymella brioniae. Didymella internal fruit rot resistance can be determined through a bio-assay, whereby young plants at 4 weeks after transplanting are sprayed for 6 weeks with a Didymella brioniae inoculum 3 times per week. Starting 3 weeks after inoculation, fruits are harvested for a period of one month, and are cut in half to observe the presence of internal fruit rot (Example 5). The pathogen usually enters the fruit through the flower, and internal fruit rot symptoms therefore start at the blossom end of the fruit, which has to be screened most thoroughly. Scoring is done as absence/presence of fruit rot; fruits having *Didymella* internal fruit rot symptoms are depicted in FIGS. 5A and 5B. A genotype is considered to be resistant when in a bioassay significantly more plants score resistant, i.e., the fruits have no internal fruit rot, than the susceptible control variety in that same bioassay. Depending on the number of plants that is used in the assay, statistical methods known to the skilled person can optionally be used to determine a significant difference. The *Didymella* fruit rot resistance of the present invention also inherits in a monogenic intermediate manner, whereby heterozygous plants, having the CNV region on only 1 chromosome, perform better than plants without the CNV region. Homozygous presence of the CNV region, on both chromosomes gives an even better resistance.

A *C. sativus* variety that is susceptible to *Pythium* and *Didymella brioniae*, and does not have the copy number variant region of the invention, is for example the hybrid variety Roxanna. This variety can be used as a susceptible control variety in a bio-assay.

A *C. sativus* genotype that has the *Pythium* resistance and *Didymella brioniae* internal fruit rot resistance of the invention is deposited as NCIMB 42776. A plant grown from NCIMB 42776, or a progeny thereof, can be used as a resistant control variety in a *Pythium* bio-assay or in a *Didymella brioniae* bio-assay. When a plant, line, or population to be assessed shows the same level of resistance as NCIMB 42776 in a bio-assay, and comprises the copy number variant region described herein, this plant, line, or population is considered to be *Pythium* resistant and *Didymella brioniae* resistant, and is therefore a plant of the invention.

A plant of the present invention is preferably a cultivated plant having improved agronomic characteristics that make it suitable for commercial cultivation. The invention also relates to a cucumber fruit harvested from a plant of the invention, wherein the cucumber fruit comprises the copy number variant region of the invention in its genome which leads to *Pythium* resistance in the plant and *Didymella brioniae* resistance in the fruit. This cucumber fruit is also referred to herein as 'the fruit of the invention' or 'the cucumber fruit of the invention'. As used herein, 'cucumber fruit' comprises a fruit produced by a plant of the species *Cucumis sativus*.

The present invention relates to a method for producing a *Pythium* and *Didymella brioniae* resistant *C. sativus* plant which comprises introducing the copy number variant region of the invention into a *C. sativus* plant.

The copy number variant region of the invention can be introduced from another plant which comprises the copy number variant region, through commonly used breeding techniques, such as crossing and selection, when the plants are sexually compatible. Such introduction can be from a plant of the same species, that usually can be crossed easily, or from a plant of a related species. Difficulties in crossing can be overcome through techniques known in the art such as embryo rescue, or cis-genesis can be applied. Suitably markers are used to follow the incorporation of the copy number variant region into another plant.

The above method can in particular be used to introduce the copy number variant region of the invention into a plant species that is suitable for incorporation of such genetic information. Said copy number variant region can be introduced from a *Cucumis sativus* plant which comprises the copy number variant region into a *Cucumis sativus* plant lacking said genetic information using standard breeding methods.

The copy number variant region of the invention can be introduced from a *Cucumis sativus* plant representative seed of which was deposited with the NCIMB under deposit number NCIMB 42776, or from the deposited seeds NCIMB 42776, or from sexual or vegetative descendants thereof. Introduction of the copy number variant region in *Cucumis sativus* leads to *Pythium* resistance and resistance to *Didymella brioniae* internal fruit rot.

A plant grown from NCIMB 42776 has the *Pythium* resistance and the *Didymella brioniae* internal fruit rot resistance of the invention, because the copy number variant region of the invention is present.

In a plant grown from NCIMB 42776, or a progeny thereof, the presence of the copy number variant region can be identified by determining the presence of at least one of the markers selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16, in particular by determining the presence of the SNP in one or more of SEQ ID NOS: 5-16 as compared to the wildtype sequence. The locations and scores of the SNPs which show the sequences of the markers that identify resistance, i.e. the B-alleles of the markers, are given in Table 2.

A plant grown from NCIMB 42776, or a progeny thereof, has two copies of an ERF gene which comprises a coding sequence represented by SEQ ID NO: 17, two copies of an ERF gene which comprises a coding sequence represented by SEQ ID NO: 18, and two copies of an ERF gene which comprises a coding sequence represented by SEQ ID NO: 19 on chromosome 3.

Alternatively the copy number variant region, of the invention can be transferred from another, sexually incompatible, plant, for example by using a transgenic approach. Techniques that can suitably be used comprise general plant transformation techniques known to the skilled person, such as the use of an *Agrobacterium*-mediated transformation method. Genome editing methods such as the use of a CRISPR/Cas system might also be employed to obtain a plant of the invention. Genome editing can be used to develop a *Pythium* and *Didymella brioniae* resistant plant through duplication of the region between SEQ ID NO: 4 and SEQ ID NO: 5, which comprises the approximately 30 genes.

The plant of the invention comprises the copy number variant region of the invention either homozygously or heterozygously.

The plant of the invention may be a plant of an inbred line, a hybrid, a doubled haploid, or a plant of a segregating population. Preferably, the plant of the invention is a non-transgenic plant.

The invention also relates to a *Cucumis sativus* seed which comprises the copy number variant region of the invention, wherein the plant grown from the seed is a plant that is resistant to *Pythium* and *Didymella brioniae*. The invention also relates to seeds produced by a plant of the invention. These seeds harbor the copy number variant region of the invention, and as such, a plant grown from said seed is a plant of the invention.

Moreover, the invention also relates to a food product or a processed food product which comprises the cucumber fruit of the invention or part thereof. The food product may have undergone one or more processing steps. Such a processing step might comprise but is not limited to any one of the following treatments or combinations thereof: peeling, cutting, washing, juicing, cooking, cooling or a salad mixture which may comprise the fruit of the invention. The processed form that is obtained is also part of this invention.

The invention also relates to propagation material suitable for producing a *Cucumis sativus* plant of the invention, wherein the propagation material is suitable for sexual reproduction, and is in particular selected from a microspore, pollen, an ovary, an ovule, an embryo sac, or an egg cell, or is suitable for vegetative reproduction, and is in particular selected from a cutting, a root, a stem cell, or a protoplast, or is suitable for tissue culture of regenerable cells, and is in particular selected from a leaf, pollen, an embryo, a cotyledon, a hypocotyl, a meristematic cell, a root, a root tip, an anther, a flower, a seed and a stem, and wherein the propagation material comprises the copy number variant region of the invention that confers *Pythium* and *Didymella brioniae* resistance. A plant of the invention may be used as a source of the propagation material.

The invention further relates to a cell of a plant of the invention. Such a cell may either be in isolated form or a part of the complete plant or parts thereof and still constitutes a cell of the invention because such a cell harbours the genetic information that leads to the *Pythium* and *Didymella brioniae* resistance of a cultivated *C. sativus* plant. Each cell of a plant of the invention carries the genetic information that leads to *Pythium* and *Didymella brioniae* resistance. A cell of the invention may also be a regenerable cell that can regenerate into a new plant of the invention. The presence of the genetic information in a cell of the invention in this context is the presence of the CNV region as defined herein.

The invention further relates to plant tissue of a plant of the invention, which comprises the CNV region of the invention. The tissue can be undifferentiated tissue or already differentiated tissue. Undifferentiated tissue is for example a stem tip, an anther, a petal, or pollen, and can be used in micropropagation to obtain new plantlets that are grown into new plants of the invention. The tissue can also be grown from a cell of the invention.

The invention moreover relates to progeny of a plant, a cell, a tissue, or a seed of the invention, which progeny comprises the CNV region of the invention that leads to *Pythium* and *Didymella brioniae* resistance. Such progeny can in itself be a plant, a cell, a tissue, or a seed.

As used herein "progeny" is intended to mean the first and all further descendants from a cross with a plant of the invention, wherein the descendant has retained the CNV region of the invention. A cross comprises a cross with another plant or a cross with itself, i.e. a selfing.

"Progeny" also encompasses a *C. sativus* plant that carries the CNV region of the invention, which plant has the *Pythium* and *Didymella brioniae* resistance of the invention, and is obtained from another plant, or progeny of a plant, of the invention by vegetative propagation or multiplication.

The invention further relates to a part of a *C. sativus* plant of the invention that is suitable for sexual reproduction and which comprises the CNV region of the invention. Such a part is for example selected from the group consisting of a microspore, pollen, an ovary, an ovule, an embryo sac, and an egg cell. Additionally, the invention relates to a part of a *C. sativus* plant of the invention that is suitable for vegetative reproduction, which is in particular a cutting, a root, a stem, a cell, or a protoplast that comprises the CNV region of the invention. The part of a plant as previously mentioned is considered propagation material. The plant that is produced from the propagation material may comprises the CNV region of the invention that leads to *Pythium* and *Didymella brioniae* resistance.

The invention further relates to tissue culture of a plant of the invention, which is also propagation material and which comprises the CNV region of the invention. The tissue culture may comprise regenerable cells. Such tissue culture can be selected or derived from any part of the plant, in particular from a leaf, pollen, an embryo, a cotyledon, a hypocotyl, a meristematic cell, a root, a root tip, an anther, a flower, a seed, and a stem. The tissue culture can be regenerated into a *C. sativus* plant which comprises the CNV region of the invention, wherein the regenerated *C. sativus* plant expresses the *Pythium* and *Didymella brioniae* resistance trait of the invention and is also part of the invention.

The invention additionally relates to the use of a plant of the invention in plant breeding. The invention thus also relates to a breeding method for the development of cultivated *C. sativus* plants that are resistant against *Pythium* and *Didymella brioniae*, wherein germplasm which comprises the CNV region for conferring said resistance is used. Seed being representative for the germplasm was deposited with the NCIMB under accession number NCIMB 42776.

The invention also concerns the use of the CNV region of the invention for the development of *Cucumis sativus* plants that have resistance to *Pythium* and *Didymella brioniae*.

The invention also relates to a marker for the identification of *Pythium* and *Didymella brioniae* resistance in a *Cucumis sativus* plant, which marker is selected from the group consisting of SEQ ID NOS: 5-16. The presence of at least one of the markers selected from the group consisting of SEQ ID NOS: 5-16, preferably the presence of at least one of the markers selected from the group consisting of SEQ ID NOS: 6-16, more preferably the presence of at least two of the markers selected from the group consisting of SEQ ID NOS: 6-16, even more preferably the presence of at least two of the markers selected from the group consisting of SEQ ID NOS: 11-16, most preferably the presence of SEQ ID NO: 13, SEQ ID NO: 14, and SEQ ID NO: 15, is indicative of the presence of resistance to *Pythium* and *Didymella brioniae*. The use of any of the markers represented by SEQ ID NOS: 5-16, preferably the use of any of the markers represented by SEQ ID NOS: 6-16, more preferably the use of any of the markers represented by SEQ ID NOS: 11-16, most preferably the use of the markers represented by SEQ ID NO: 13, SEQ ID NO: 14, or SEQ ID NO: 15, for identification of *Pythium* and *Didymella brioniae* resistance in a *Cucumis sativus* plant is also part of the invention. All these markers can also be used to develop other markers for the identification of the CNV region of the invention leading to *Pythium* and *Didymella brioniae* resistance, which use is also part of the present invention.

The present invention also relates to a method for selecting a *Pythium* and *Didymella brioniae* resistant *Cucumis sativus* plant, which comprises determining the presence of the copy number variant region of the invention, and selecting a plant that comprises the copy number variant region of the invention as a *Pythium* and *Didymella brioniae* resistant plant.

The invention also relates to a method of testing a *Cucumis sativus* plant for the presence of the copy number variant region of the invention conferring *Pythium* and *Didymella brioniae* resistance in its genome, which comprises detecting a marker sequence selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16, or detecting any combination thereof, in the genome of the *Cucumis sativus* plant.

In one embodiment of the invention, the method of testing a *Cucumis sativus* plant for the presence of the copy number variant region of the invention conferring *Pythium* and *Didymella brioniae* resistance in its genome further may comprise selecting a *Cucumis sativus* plant that comprises the copy number variant region of the invention in its genome as a *Pythium* and *Didymella brioniae* resistant plant.

The invention also relates to a method for the production of a *Cucumis sativus* plant which is resistant against *Pythium* and *Didymella brioniae*, said method which comprising:

a) crossing a plant of the invention with a plant not comprising the CNV region of the invention, to obtain an F1 population;

b) optionally performing one or more rounds of selfing and/or crossing a plant from the F1 to obtain a further generation population;

c) selecting from the population a plant that comprises the CNV region and is resistant against *Pythium* and *Didymella brioniae*, suitably by using a molecular marker linked to the CNV region of the invention.

The marker of step c) of the method can be a marker represented by any of SEQ ID NOS: 5-16, preferably by any of SEQ ID NOS: 6-16, more preferably by any of SEQ ID NOS: 11-16, most preferably by SEQ ID NO:13, SEQ ID NO:14, or SEQ ID NO:15. The plant can also be phenotypically selected for having resistance to *Pythium* or *Didymella brioniae*.

The plant of the invention used in the method for the production of a *Cucumis sativus* plant which is resistant against *Pythium* and *Didymella brioniae* is optionally a plant grown from seed deposited under NCIMB accession number 42776, or progeny thereof.

The invention additionally provides for a method of introducing another desired trait into a *Cucumis sativus* plant which comprises *Pythium* and *Didymella brioniae* resistance, which comprises:

a) crossing a *Cucumis sativus* plant of the invention with a second *Cucumis sativus* plant that comprises the other desired trait to produce F1 progeny;

b) selecting an F1 progeny that comprises *Pythium* and *Didymella brioniae* resistance and the other desired trait;

c) crossing the selected F1 progeny with either parent, to produce backcross progeny;

d) selecting backcross progeny which comprises *Pythium* and *Didymella brioniae* resistance and the other desired trait; and e) optionally repeating steps c) and d) one or more times in succession to produce selected fourth or higher backcross progeny that comprises the other desired trait and has resistance to *Pythium* and *Didymella brioniae*.

The plant of the invention used in the method of introducing another desired trait into a *Cucumis sativus* plant which comprises resistance to *Pythium* and *Didymella brioniae* is optionally a plant grown from seed deposited under NCIMB accession number 42776, or progeny thereof.

Optionally, selfing steps are performed after any of the crossing or backcrossing steps in the described method. Selection of a plant which comprises *Pythium* and *Didymella brioniae* resistance and the other desired trait can alternatively be done following any crossing or selfing step of the method. The desired trait can be selected from, but is not limited to, the following group: resistance to bacterial, fungal or viral diseases, insect or pest resistance, improved germination, plant size, plant type, improved shelf-life, water stress and heat stress tolerance, and male sterility. The invention includes a *Cucumis sativus* plant produced by this method and the *Cucumis sativus* fruit obtained therefrom.

The invention further relates to a method for the production of a *Cucumis sativus* plant which comprises the CNV region of the invention that leads to resistance to *Pythium* and *Didymella brioniae*, by using tissue culture of plant material that comprises the CNV region of the invention in its genome.

The invention further relates to a method for the production of a *Cucumis sativus* plant which comprises the CNV region of the invention that leads to resistance to *Pythium* and *Didymella brioniae*, by using vegetative reproduction of plant material that comprises the CNV region of the invention in its genome.

The invention further provides a method for the production of a *Cucumis sativus* plant having resistance to *Pythium* and *Didymella brioniae* as defined herein by using a doubled haploid generation technique to generate a doubled haploid line that homozygously comprises the CNV region of the invention and is resistant against *Pythium* and *Didymella brioniae*.

The invention further relates to a method for the production of a *Cucumis sativus* plant which comprises the CNV region of the invention wherein said CNV region of the invention leads to *Pythium* and *Didymella brioniae* resistance, which method comprises growing a seed which comprises the CNV region of the invention into the said *Cucumis sativus* plant. The seed used in the method is optionally seed deposited with the NCIMB under deposit number 42776, or progeny seed thereof.

The invention further relates to a method for seed production which comprises growing a *Cucumis sativus* plant from seed of the invention, allowing the plant to produce fruits with seed, and harvesting those seed. Production of the seed is suitably done by crossing or selfing. Preferably, the seed that is so produced has the capability to grow into plants that are resistant to *Pythium* and *Didymella brioniae*.

The invention further relates to hybrid seed and to a method for producing said hybrid seed, which comprises crossing a first parent plant with a second parent plant and harvesting the resultant hybrid seed, wherein the first parent plant and/or the second parent plant is a plant of the invention. The resultant hybrid plant which comprises the CNV region of the invention and which exhibits resistance to *Pythium* and *Didymella brioniae* is also a plant of the invention.

It is clear that the parent that provides the trait of the invention is not necessarily a plant grown directly from the deposited seed. The parent can also be a progeny plant from the deposited seed, or a progeny plant from seed that is identified to have obtained the trait of the invention by other means.

Introgression of the CNV region of the invention as used herein means introduction of the CNV of the invention from a donor plant which comprises said CNV region into a recipient plant not carrying said CNV region by standard breeding techniques wherein selection for plants which comprise the CNV region of the invention can be performed phenotypically by means of observation of the resistance to *Pythium* or *Didymella brioniae*, or selection can be performed with the use of markers through marker assisted breeding, or combinations of these. Selection is started in the F1 or any further generation from a cross between the recipient plant and the donor plant, suitably by using markers as identified herein by SEQ ID NOS: 5-16. The skilled person is familiar with creating and using new molecular markers that can be used to identify or are linked to the trait of the invention. Development and use of such markers for identification and selection of plants of the invention is also part of the invention.

The phrase "trait" in the context of this application refers to the phenotype of the cultivated *Cucumis sativus* plant. In particular, the word "trait" refers to the trait of the invention, more in particular to the resistance to *Pythium* and *Didymella brioniae*. When a cultivated *C. sativus* plant exhibits the trait of the invention, its genome may comprise the CNV region of the invention causing the trait of the invention. Hence, the "trait of the invention" as used herein is intended to refer to the trait of resistance to *Pythium* and *Didymella brioniae* caused by the CNV region of the invention.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Bio-Assay for *Pythium* Resistance and Deposit Development in *C. Sativus*

A *Pythium* resistant *Cucumis sativus* source that was identified in a germplasm screen was first crossed with various internal breeding lines to create a number of backgrounds in which the resistance would be present. These crosses were put through several cycles of backcrossing and inbreeding to develop cultivated lines that have commercially acceptable standards. During this process, continuous selection for *Pythium* resistance was done, since the resistance was not uniformly present in the source, and to make sure the resistance was not lost in the process.

Selection for *Pythium* resistance was done with a bio-assay. Plants were sown in trays filled with potting soil in a greenhouse under normal cucumber growing conditions, at a day temperature of around 23° C. Seven days after sowing, multiplication of the *Pythium* pathogen was started on standard agar plates containing oatmeal medium. At 14 days after sowing the inoculum was prepared by blending around 2 agar plates of the *Pythium* with one liter of water. The seedlings were taken out of the soil and dipped in the inoculum for around 5 minutes. After inoculation plants were replanted in pots with regular potting soil. Assessment for resistance was done 14 days after inoculation, whereby each plant was scored in 2 categories: 0 (resistant) and 1 (dead/wilted). At least 2 replicates of 10 plants were done for each assay. Because the scores can vary somewhat depending on the conditions, it is essential that sufficient susceptible control plants are included to verify the intensity of the test. When the average number of plants that is resistant in a certain population was statistically higher than the number of resistant plants in the susceptible control in the same experiment, this population was considered to be resistant. However, if the difference was not very convincing the experiment would be repeated to confirm the presence of the resistance.

After several uniform lines were obtained in which the disease resistance did not segregate anymore, these lines were crossed again with internally developed *Pythium* susceptible breeding lines. Again, backcrossing and some inbreeding was done to develop improved material with *Pythium* resistance. From two segregating populations, one based on a cross with susceptible internal line 021, and one based on a cross with susceptible internal line 029, DH lines were created to obtain completely homozygous lines in which the resistance could be optimally assessed. DH line 002 from the combination with line 021 was selected, and DH lines 027 and 053 from the combination with line 029 were selected. All three lines showed a good level of *Pythium* resistance

TABLE 1

*Pythium* bio-assay in *C. sativus* lines.

| Number | Line | | Pythium plant score R/S | Pythium line score |
|---|---|---|---|---|
| 15175 | DH | 1138 | 8/4 | R |
| 15224 | R source | 1137 - R control | 10/2 | R |
| 15223 | S line | 021 | 0/12 | S |
| 15226 | DH | 002 - F1BC3 with line 21 | 4/3 | R |
| 15320 | DH | 002 - F1BC3 with line 21 | 6/0 | R |
| 11099 | F1 | VENTURA - S control | 0/12 | S |
| 11100 | DH | 1138 | 6/0 | R |
| 11245 | R source | 1137 - R control | 12/0 | R |
| 11401 | R source | 1137 - R control | 10/2 | R |
| 11400 | DH | 021 | 2/10 | S |
| 11244 | DH | 021 | 6/6 | S |
| 11246 | DH | 002 - F1BC3 with line 21 | 11/1 | R |
| 11402 | DH | 002 - F1BC3 with line 21 | 12/0 | R |
| 13007 | F1 | VENTURA - S control | 2/10 | S |
| 13008 | R source | 1137 - R control | 12/0 | R |
| 13010 | R source | 1137 - R control | 12/0 | R |
| 13097 | R source | 1137 - R control | 11/1 | R |
| 13028 | S line | 029 | 0/12 | S |
| 13115 | S line | 029 | 0/12 | S |
| 13048 | DH | 027 - F2BC1 with line 29 | 8/4 | R |
| 13135 | DH | 027 - F2BC1 with line 29 | 8/4 | R |
| 13064 | DH | 053 - F2BC1 with line 29 | 10/2 | R |
| 13151 | DH | 053 - F2BC1 with line 29 | 10/2 | R |

Crosses were made between line 002 and line 027, and between line 002 and line 053. All resulting seeds were homozygous for *Pythium* resistance. Seeds of the crosses were deposited under accession number NCIMB 42776.

Example 2: QTL Mapping and Marker Development

In order to map the *Pythium* resistance conferring QTL of the invention, two populations from the 1137 source in combination with susceptible internal breeding lines were developed through backcrossing and selfing. Both populations, having the same source but different backgrounds, were subsequently crossed with susceptible line 021 to develop further backcross populations that represent cultivated cucumber plants. From one population, a final BC4F1 was taken, and from the other population a BC3F1.

From the BC4F1 population and the BC3F1 population DH lines were generated using standard DH generation techniques for *C. sativus*. In this way homozygous lines could be obtained that are most suitable for mapping purposes.

From the BC4F1 population 42 DH lines were genotyped and phenotyped for *Pyhtium* resistance. From the BC3F1 population 43 DH lines were genotyped and phenotyped. A total of 9 highly resistant *Pythium* lines were selected for further breeding. Phenotyping was done as described in Example 1. Susceptible and resistant parents were also genotyped and phenotyped in the same way. Phenotypic scores were used as input for the mapping.

Genotype data for the 85 DH lines and their parents were obtained starting with an internal set of 66 SNP markers. A good linkage map was obtained covering all 7 *C. sativus* chromosomes wherein the markers were relatively equally represented. Because all material was homozygous, only A and B scores were given, indicating the presence of either the allele from the resistant source or the allele from the susceptible cultivated background.

QTL analysis was performed, and mapping of the data resulted in the identification of a QTL on chromosome 3 that still covered a relatively large area between 8.3 and 46.1 cM. To zoom in within this region a larger number of SNP markers known to be located in this stretch were used for further genotyping, resulting in finemapping of the QTL. The markers that resulted from the QTL analysis after finemapping as flanking the QTL on chromosome 3 are indicated with SEQ ID NO: 1 and SEQ ID NO: 2. SEQ ID NO: 1 flanks the region but also co-segregates with the QTL and allele B is therefore linked to the QTL conferring resistance. SEQ ID NO: 2 flanks the region and is indicative for the position of the QTL, but depending on the background allele B will be present in the resistant background, but the susceptible background can score either the A or the B allele.

The mapping of this population also resulted in the identification of a number of polymorphic SNP markers that can be used to identify the presence of the QTL on chromosome 3. The SNP markers resulting from mapping of this population that are linked to the resistance conferring QTL are indicated as SEQ ID NOS: 3, and SEQ ID NOS: 5 to 16. The sequence of these markers, as well as their genetic position on the genetic map and corresponding physical positions on the publicly available *C. sativus* genome reference sequence based on Cs9930 are listed in Table 2. Thus these markers may be used to identify individuals of other populations that comprise the resistance conferring QTL on chromosome 3 in their genome.

In the deposit NCIMB 42776, the presence of the QTL and the *Pythium* resistant genotype is linked to SNP markers with SEQ ID NO: 1, SEQ ID NO: 3, and SEQ ID NOS: 5-16. These SNP sequences can be used as molecular markers for identifying *Pythium* resistant plants grown from said deposit. Furthermore, since the markers were also positioned on the *C. sativus* public genome map and the actual physical positions determined (Table 2), these markers may be used to identify the presence of the QTL on chromosome 3 in any other population that comprises said QTL.

Table 2 depicts SNP marker sequences and locations.

H>B indicates a heterozygous CNV marker, which are the markers represented by SEQ ID NO: 6, SEQ ID NO: 7, SEQ ID NO: 8, SEQ ID NO: 9, SEQ ID NO: 14, SEQ ID NO: 15, and SEQ ID NO: 16. One copy of the CNV region has the SNP score of the susceptible background for these markers, the other copy of the CNV region has a SNP unique to the resistant background and therefore the presence of the CNV region. When running the marker assay for a H>B marker, a score AA means there is a homozygous presence of the A allele—the CNV region is not present, and the plant is susceptible. When the score is AABB, it means the CNV region is present and the plant is resistant. In this situation, the AABB score therefore indicates the homozygous presence of the B allele. Because normally an AABB score would be viewed as heterozygous, the marker is called herein a 'heterozygous CNV marker', and the score is indicated below as H>B'.

A plant heterozygous for the presence of the CNV region scores AAB for heterozygous CNV markers—an A score for the chromosome without the CNV region, i.e. the A allele, and an AB score for the chromosome with the CNV region, i.e. the B allele. For homozygous CNV markers, which are markers represented by SEQ ID NO: 10, SEQ ID NO: 11, SEQ ID NO: 12, and SEQ ID NO: 13, the heterozygous presence of the CNV region gives an ABB score. This AAB or ABB score represents the H (heterozygous) presence of both an A and a B allele, and is present in a plant that is heterozygous for *Pythium* resistance.

The B allele of the SNPs in the sequences below, which is the allele as presented in column 2 of the Table, is present in the *Pythium* resistant plant.

TABLE 2

SNP marker sequences and locations.

| Marker name | Sequence; indicating the SNP | Position of the SNP in the sequence and type of SNP (alleles A/B) | Position of the SNP in the public *C. sativus* genome 9930 V2 |
|---|---|---|---|
| SEQ ID NO: 1 | TGGCTCCTGATCGTGGTGCCACAGTCCCAA AATTTGGTGACTGGGACGAAAGCGATCCA TCGTCATCTGAGAACTGCACTAATATTTTCA CCAGAGTGCGTGTGGAGAGACAAACGGAA GACGGAAGTTTGCCAGCTGGGACCAATGT TTCTAGTATTCGTAGTCGTTCTAGTGCCGA AAACTCAAAGAGATGTTGCTGTT | 101 C/T | 8423638 |
| SEQ ID NO: 2 | ATTAAACTTTATGAAGGTTTCCCTTTTTATCT TTCCTTTATCCAACAAATAAATTCTTATTTAC AACTCCACAAACTTAATTATATCCCAATTTG GTATCTTTCAATCTTCTTCCTCTTAAACAGCA ACTTGGGCTGCAGCCAATCTTGCTACCGGA ACTCTGAAAGGAGAACAAGAAACATAGTCA AGTCCAGCCTCAGC | 101 C/T (flanking the QTL region; score B can also be present in a susceptible plant) | 10261179 |
| SEQ ID NO: 3 | TAATAAAACATTATATATATATTTRCATCAA ATATATATAAATTAAAAAAAATTAAATAGAC TCGTAAGAAAGGTGTAAATCAAATAACAAA | 101 A/G | 9082698 |

TABLE 2-continued

SNP marker sequences and locations.

| Marker name | Sequence; indicating the SNP | Position of the SNP in the sequence and type of SNP (alleles A/B) | Position of the SNP in the public *C. sativus* genome 9930 V2 |
|---|---|---|---|
| | AAAATTTTGAAATAAATTTAACTCACTTCTT ATCTTATTCAATTATTTTATCTTGCATGAAAT TTTGTTAAGAATAATAGTTTKTATATTTAGA GATCKRTTAAKATTT | | |
| SEQ ID NO: 4 | GATACGAAACTGTCTTTAATTATTTAAACTT GAGTGTGGATCAAAAACACATTTACAATAG TCGTTAAAGATTAGAGAAAGCTTGGATTTT AGGAATTAAAGATTTCAAACCATTATTTGGT CACTTTGGTAGGATTGCAAGCTTCAAGAGG ACTTGACAGATGAAATGGTTGGTTTAGCAA AGCAGTCGAAGAGAGCAGTCTGATAACGA GCCAATCCTTAGAGAGCATTGAGAAAGTAT ATTTTCTCTACTAATCGTTCATTGCTGACGTA GTAGATATAGAAATTTTATACCTTTGGTTTC TTCAAAATATAAACAAACGCTATAGAAATTA AAATAGGAAAGTCTTCGATTCGTCCCATATT CAAAGCATAGTTTGAGCAATTCTGTTTTCA GTG | 212 A/G (flanking the CNV region; score B can also be present in a susceptible plant) | 9138798 |
| SEQ ID NO: 5 | ATTTTAATCTAATAGAGAGTGATTAACTCAT GCTAGGCACATTTTAATAATCATATTAACTG CATTCTAATTTAACAATGTAAAATGACTTTTA TTATACCTATTTGGAGAATTTTGTTATTTTAT TATTATTGTTTTTTTTTACTACACAATTTTCAT TTAAATAACCAGAAAAATGATTGACTTCCAC TATTTTAAAAA | 101 T/C | 9294008 |
| SEQ ID NO: 6 | AAATATTTCCATATACGTGTAGGCAATGGTG GTAAATACCTAGAGGCGTCAAGATCCAATC ATAGGAGCACAGCGATCTCAACTATTTTGTG GTTGCRCCGGAAAATGGGNNNNNNNNNNN NTGAGGATGAGGAAGAGGAGAGGGAGGG GCTATGGAGAGAAATGGGGGAGGAGGTGA TGGGGATATTTAAGAA | 122 G/T H > B | 9175772 |
| SEQ ID NO: 7 | ATATCAGAAGAAAAAAAATAGACTGAATTA ATCATGGATTTTGAAAAACTTTTTTTTTTTTC AAGTAATATATTCTTAAGAAACCTTTAGAAT CCATTTTGCATAAAATGACATTCTTTTTTATT TACATTTGGAAAAATACCATTTTTTTATTCAA ATGAAAATTATGAAAAATAGCTAAATAAAT AAAATATT | 48 C/AC H > B | 9188302 |
| SEQ ID NO: 8 | GTCCTTTATAAAAAATTTGAAACGTAAATAG TTGGATTTTCTNAAAAAAAAAATAGAGAC TATGTGTCATTTATATCATGTCAATAAGATG GTCTAGAA | 51 C/A H > B | 9188499 |
| SEQ ID NO: 9 | AAGCAACCTATTAATTATTCTATTGAGGGTA GCAGATTCCATCTTAGAGTTCCTGCTTCAAT CCAAGTGAAAAAAGAAAAAAGAAAAAAGA AAAWAANATCATTCAGATCAAACAAAATAG CAGTAGTAAAGTAAAAAGAAAAAAAAAAAA AAAAAAAGCAGAATAAAGGCAGCAACGTA CTTGGATGTTGAGGGG | 99 T/A H > B | 9193352 |
| SEQ ID NO: 10 | NACACACACACACATTATCAAGCAAAAC ATCACTAATTCCAAATGATAATTGTGTAACA TTAATTGAAAATTCCACATGAAAAACTGAA AGAATGAATTGACATCACACTCTATTATAAT ATATATGAACTGCTTTCTTAATTCTCAATTAG TTTTGAGATAAAAATAAATATATTAA | 101 C/T | 9195431 |
| SEQ ID NO: 11 | TATTATTGGAAATGATTTTGATTTTGAATAN AAAAAAGGTGAGATCCATGTTATGTATACA TTACAATCAAATGATAAAYAATGAATTAATG TGTGGAATGATGCAATCTAAAATTTTGGAC ATGCACAAAATAGAAAACATCATGCATCNN NNNNNNNNNNNNNNTACATATACTTTTAG AACAACCTTCCATCAAAT | 101 C/C | 9196292 |

TABLE 2-continued

SNP marker sequences and locations.

| Marker name | Sequence; indicating the SNP | Position of the SNP in the sequence and type of SNP (alleles A/B) | Position of the SNP in the public C. sativus genome 9930 V2 |
|---|---|---|---|
| SEQ ID NO: 12 | TAAAAAATGTTAGATAACAAATGACAGCTA GAAAATAAATTAGTATTTTATCTTATATGAG TTTTTTTTTTTTTTTTAAAAATATCTTCTTCTA AGAAATGAAATTATTTTCCTTTTTAGAAATTT CTAAAATTTAGGAAATCAAATTATTCTCCCT TTTCAAATCTTTAAAATTTAGGACGTAAATA ATTTGATATTTGG | 101 C/G | 9201783 |
| SEQ ID NO: 13 | TTATGTAAAATATCAAATACAAAAGTGAAA ATATAGAAATTATTCGTGTGATAACTTACTA ATTTCAATACATTTAAGGTTAAAATTTTAATT ATTATTTCAAAGAAGTATTGTTTACCTCAAG GAAGAATCTTACATGAATCAATAATCATTGG TCTTATGATTAATCTTTTTTTCTTTCGAAACA TTT | 101 G/C | 9216644 |
| SEQ ID NO: 14 | GGGCACTGATATAGCCAAAGCTATCCCTCC AATTGGTRATGGCTGCAGAGTACAGATCGA AATTACTATTGTAAATCAAAGGTTTGGTGAG GTCGCGAGTTTAATATTGTTTCTTGGATTCG GTTTCTTGCTCGTGAAATCTTCGAACTGCAT CTTTCATCTCCTCAAGAACGTTCTCCGGAAT CCCATGGTTAATCAGTT | 101 G/T H > B | 9257623 |
| SEQ ID NO: 15 | TCACAATGAATTCTTTTTTTATTTGAARAACA TCTATTAGAAAGACTGTTTATCATGATCCCT TCCCTTCAGGTACCACCCATGGGTTTATTCTT CCCAACGCTTTTGGTTCCAGATGTGTATCCA CCACCACCCCGTGCATGGTCAGTTGCTAATA ATCATATTCAACTAGTTTTCATGTCAAAATAT ACCTGTATGATG | 101 T/C H > B | 9273716 |
| SEQ ID NO: 16 | TAAAMAGAGCCATAAAGTAATCAGGTAGA GTTAAACCCAGATCCAACTCCCGCATGTACA GGACCCCCCGATCGCTCCTCATGATCAAATA GTCATGGCTGAGTGCCAATGTAAAGCCAGC GGCAGCAGCGTGTCCTGTAATGGCAGCAAT GGTAGGCATAGGAAGGGAAATGARTTCGG CAACGACGGACTTGAAGATCT | 101 C/G H > B | 9279567 |

FIG. 2 shows a representation of the position of the markers and the scoring for the homozygous and heterozygous CNV markers.

Example 3: Identification of the Copy Number Variant Region within the QTL

Whole genome sequencing data of various *Cucumis sativus* lines, including material with *Pythium* resistance were mapped and subsequently analyzed using WGS read alignment visualization tools. After this, the sequence read data were aligned and compared against an internally generated reference genome sequence of *Cucumis sativus*. It was then determined that within the QTL region on chromosome 3 that was indicative for *Pythium* resistance, a stretch could be found wherein the read depth indicated the presence of multiple copies. This meant a copy number variant (CNV) region was present in the QTL.

Marker assays combined with the CNV information resulted in markers that were flanking the CNV, and could therefore be used to indicate the position of the CNV region. These flanking CNV markers are represented by SEQ ID NO: 4 and SEQ ID NO: 5. Because they are not within the CNV region, they score with just two alleles—A or B. Within the CNV region, around 30 annotated genes are present.

To determine if this CNV region was related to the *Pythium* resistance, markers were designed to identify SNPs that were present within this region. Since within the CNV region each sequence is present twice, also a double marker score would be observed. It was found that several SNPs were present in one copy of the CNV region, but the other copy would have the same sequence as the reference or susceptible, i.e. the wildtype, genome. The scoring of these markers was rather difficult, since the sequence of the wildtype, which is indicated herein as allele A, is present twice, while the sequence of the SNP that is present in one copy of the CNV in the resistant material is also present twice. The SNP sequence relating to the resistant material is indicated as allele B. This results in an 'AABB' marker score to indicate the homozygous presence of the CNV region. These markers are the 'heterozygous CNV markers'.

The markers that scored in this way are represented by SEQ ID NO: 6, SEQ ID NO: 7, SEQ ID NO: 8, SEQ ID NO: 9, SEQ ID NO: 14, SEQ ID NO: 15, and SEQ ID NO: 16.

In addition to these markers, however, also SNPs could be identified that were present in both copies of the CNV region. These markers, again scored double because of the presence of the two copies, would have a BBBB score when the CNV region is homozygously present in a plant. These markers are called herein the 'homozygous CNV markers'.

The markers that score in this way are represented by SEQ ID NO: 10, SEQ ID NO: 11, SEQ ID NO: 12, and SEQ ID NO: 13.

FIG. 2 shows the position and the scoring of these and other markers for *Pythium* resistance.

Next it was determined if the marker scores that indicated the presence of the CNV region were co-segregating with, and therefore linked to and indicative of, *Pythium* resistance. It was indeed found that the presence of the CNV region in a plant was indicative of *Pythium* resistance of that plant. It was therefore concluded that the presence of the CNV region leads to *Pythium* resistance in *Cucumis sativus*.

Example 4: ERF Gene Expression of *Pythium* Infected *C. Sativus* Plants

The CNV region that was identified to be linked to *Pythium* resistance comprises 30 genes, 3 of which were designated to be ERF genes. To determine the expression levels of these 3 ERF genes within the CNV region on chromosome 3 in cucumber, an expression analysis was performed. For this experiment the expression of these genes in plants of the invention, represented by plants of deposit NCIMB 42776, was compared with the expression in plants of the *Pythium* susceptible hybrid cucumber variety Roxanna as a control.

For both genotypes of plants of the invention and the control variety 3 plants were treated with *Pythium* infection according to the protocol described in Example 1. To facilitate *Pythium* infection, the roots were wounded before dipping them in the inoculum. As a control for the treatment, of each genotype also 3 plants were used as control, undergoing the same treatment including wounding of the roots, but without actual *Pythium* infection.

Subsequently, for each plant 3 stem-samples and 1 root-sample were taken and RNA was extracted. qPCR primers were designed for all 3 ERF genes to detect the expression. All samples were tested by performing the qPCR using SYBR-green and a relative expression analysis was performed. Results of the averages of the stem samples are presented in Table 3.

TABLE 3

ERF relative gene expression comparison between resistant and susceptible plants

| | Pythium | ERF1B | ERF098 | ERF096 |
|---|---|---|---|---|
| ROX | − | 0.0399 | 0.2926 | 0.0584 |
| GBN | − | 0.1129 | 1.4026 | 1.3386 |
| ROX | + | 1.0505 | 0.3470 | 4.7459 |
| GBN | + | 2.0048 | 5.5484 | 7.4518 |

The treatment without *Pythium* infection is indicated with a '−'; when *Pythium* infection was present it is indicated with a '+'. 'GBN' are Pythium resistant plants of the invention; 'ROX' are plants of susceptible control variety Roxanna. ERFIB is the gene represented by SEQ ID NO: 17; ERF098 is the gene represented by SEQ ID No 18; ERF096 is the gene represented by SEQ ID NO: 19.

The experiment showed that the expression of each ERF gene was clearly higher in the resistant plants than in the susceptible control variety. The results are also graphically presented in FIG. 4. Expression was increased when *Pythium* infection was present, but also non-infected GBN plants showed a higher expression for all genes than the susceptible control variety. The analysis to determine increased expression can therefore be performed both with and without disease pressure.

Example 5: *Didymella* Brioniae Internal Fruit Rot Resistance of *C. Sativus* Plants Having the CNV Region

*Cucumis sativus* plants of a uniform breeding line (line 468) that showed susceptibility to *Didymella brioniae* were backcrossed with a *Cucumis sativus* donor plant in which the copy number variant (CNV) region, described in Example 3, was introgressed. This plant was already determined to be resistant to *Pythium* due to the presence of the CNV region. Since the whole CNV region was present, all markers of SEQ ID NOS:6-16 were also present in this donor plant. The CNV region was the same CNV region as found in NCIMB 42776. Backcrossing was traced with markers to accommodate easy selection of plants comprising the CNV region.

A near-isogenic line was obtained (line 469), which was the same as the breeding line, but having the CNV region, which is the same as found in NCIMB 42776, introgressed. Subsequently, a bio-assay for *Didymella brioniae* was performed on the original breeding line (468), and the near-isogenic line with the CNV introgressed through backcrossing (469), to determine the contribution of the CNV region to *Didymella* internal fruit rot.

Seeds of the susceptible line and the near-isogenic CNV-introgressed line were sown, and 14 seedlings were transplanted after 3 weeks in a randomized design. Starting at 4 weeks after transplanting, the young plants were sprayed with a *Didymella brioniae* spore suspension having a concentration of 100,000 spores per mL. Spraying was done 3 times per week, for 6 weeks, using a Birchmeier backpack sprayer. Starting 3 weeks after inoculation, fruits were harvested 1 or 2 times per week, depending on the number of fruits, for a period of 1 month. To determine the presence of *Didymella* internal fruit rot, the fruits were cut in half lengthwise, at the side of the blossom end. Since *Didymella brioniae* usually enters the fruits through the flower, the fruit rot manifests itself starting on the blossom end of the fruit, as a typical rustbrown rot. Cucumber fruits assayed in this way, which show *Didymella* internal fruit rot, are depicted in FIGS. 5A and 5B.

From line 468, a total of 314 fruits were harvested and assayed, while from line 469, 321 fruits were harvested and assayed. The results showed a remarkable and convincing difference, whereby the percentage of infected fruits was decreased from 126, which is 40% of the total, in line 468 to only 42, which is 13% of the total, in line 469 (Table 4). It was thus determined that the incorporation of the CNV region in a *Didymella brioniae* susceptible *Cucumis sativus* plant leads to increased resistance to *Didymella* internal fruit rot.

TABLE 4 bio-assay for Didymella internal fruit rot

| Line | Description | #observed fruits | #fruits with internal fruit rot | % fruits with internal fruit rot |
|---|---|---|---|---|
| 468 | internal breeding line, S | 314 | 126 | 40% |
| 469 | near-isogenic line with CNV | 321 | 42 | 13% |

The invention is further described by the following numbered paragraphs:

1. A *Cucumis sativus* plant comprising a QTL on chromosome 3 between SEQ ID No. 1 and SEQ ID No. 2, the presence of which QTL leads to resistance against *Pythium*.

2. A *Cucumis sativus* plant of paragraph 1, wherein the *Pythium* resistance is due to the presence of a copy number variant region within the QTL, which copy number variant region is flanked by SEQ ID No. 4 and SEQ ID No. 5.

3. A *Cucumis sativus* plant of paragraph 2, wherein the presence of the copy number variant region can be identified by determining the presence of at least one of the markers selected from the group consisting of SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, and SEQ ID No. 16.

4. A *Cucumis sativus* plant of any of the paragraphs 1-3, wherein the *Pythium* resistance is due to the presence of at least two copies of an ERF gene within the copy number variant region, and/or a mutant ERF gene within the copy number variant region.

5. A *Cucumis sativus* plant of paragraph 4, wherein the presence of the at least two copies of an ERF gene and/or the mutant ERF gene leads to increased expression of said ERF gene.

6. A *Cucumis sativus* plant of any of the paragraphs 1-5, wherein the QTL, or the copy number variant region, or the at least two copies of an ERF gene is as comprised in the genome of a *Cucumis sativus* plant representative seed of which was deposited with the NCIMB under deposit number NCIMB 42776.

7. Propagation material suitable for producing a *Cucumis sativus* plant of any one of the paragraphs 1-6, wherein the propagation material is suitable for sexual reproduction, and is in particular selected from a microspore, pollen, an ovary, an ovule, an embryo sac, or an egg cell; or is suitable for vegetative reproduction, and is in particular selected from a cutting, a root, a stem, a cell, a protoplast; or is suitable for tissue culture of regenerable cells, and is in particular selected from a leaf, pollen, an embryo, a cotyledon, a hypocotyl, a meristematic cell, a root, a root tip, an anther, a flower, a seed, or a stem, and wherein the propagation material comprises the QTL as defined in paragraph 1, or the copy number variant region as defined in paragraph 2 or 3, or the two copies of an ERF gene within the copy number variant region as defined in paragraph 4, or the mutant ERF gene as defined in paragraph 4 or 5.

8. Marker for the identification of *Pythium* resistance in a *Cucumis sativus* plant, which marker is selected from the group consisting of SEQ ID Nos. 1-16.

9. Use of a marker of paragraph 8 for identification of *Pythium* resistance in a *Cucumis sativus* plant.

10. Method for producing a *Pythium* resistant *Cucumis sativus* plant comprising introducing a QTL as defined in paragraph 1, or introducing a copy number variant region as defined in paragraph 2 or 3, or introducing at least one extra copy of an ERF gene as defined in paragraph 4, or introducing a mutant ERF gene as defined in paragraph 4 or 5.

11. Method for selecting a *Pythium* resistant *Cucumis sativus* plant, comprising determining the presence of the QTL as defined in paragraph 1, or the copy number variant region as defined in paragraph 2 or 3, or determining the presence of at least two copies of an ERF gene or of a mutant ERF gene as defined in paragraph 4 or 5, and selecting a plant that comprises the QTL, or the copy number variant region, or the at least two copies of an ERF gene or the mutant ERF gene as a *Pythium* resistant plant.

12. Seed, wherein the seed comprises the QTL as defined in paragraph 1, or the copy number variant region as defined in paragraph 2 or 3, or the at least two copies of an ERF gene or the mutant ERF gene as defined in paragraph 4 or 5.

13. A method for producing a *Cucumis sativus* plant which is resistant against *Pythium*, said method comprising:
 a) crossing a plant of any one of the paragraphs 1-6 with another plant to obtain an F1 population;
 b) optionally performing one or more rounds of selfing and/or crossing a plant from the F1 to obtain a further generation population;
 c) selecting from the population a plant that comprises the QTL as defined in paragraph 1, or the copy number variant region as defined in paragraph 2 or 3, or the at least two copies of an ERF gene a mutant ERF gene as defined in paragraph 4 or 5, which plant is resistant against *Pythium*.

14. The method of paragraph 13, wherein the plant of any one of the paragraphs 1-6 is a plant grown from seed deposited under NCIMB accession number 42776, or from progeny thereof.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A *Cucumis sativus* plant comprising a copy number variant region on chromosome 3, wherein the copy number variant region is flanked by SEQ ID NO: 4 and SEQ ID NO: 5, and
wherein the copy number variant region comprises markers comprising the sequences of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16, which sequences are the B-alleles of said markers, and
wherein representative seed of a *Cucumis sativus* plant comprising the copy number variant region was deposited under NCIMB Accession No. 42776, and
wherein the presence of the copy number variant region confers *Pythium* and *Didymella brioniae* resistance.

2. A *Cucumis sativus* plant as claimed in claim 1, wherein the presence of *Pythium* and *Didymella brioniae* resistance is identified by determining the presence of at least one of the markers selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

3. A *Cucumis sativus* plant as claimed in claim 2, wherein the presence of *Pythium* and *Didymella brioniae* resistance is identified by determining the presence of at least one of the markers selected from the group consisting of SEQ ID NO: 11, SEQ ID NO: 12, SEQ ID NO: 13, SEQ ID NO: 14, SEQ ID NO: 15, and SEQ ID NO: 16.

4. A *Cucumis sativus* plant as claimed in claim 3, wherein the presence of *Pythium* and *Didymella brioniae* resistance is identified by determining the presence of at least one of the markers selected from the group consisting of SEQ ID NO: 13, SEQ ID NO: 14, and SEQ ID NO: 15.

5. A propagation material having the copy number variant of the *Cucumis sativus* plant of, and for producing the *Cucumis sativus* plant of, claim 1,
wherein the propagation material is suitable for sexual reproduction, or is suitable for vegetative reproduction, or is suitable for tissue culture of regenerable cells.

6. The propagation material of claim 5, wherein the propagation material is suitable for sexual reproduction and is a microspore, pollen, an ovary, an ovule, an embryo sac, or an egg cell.

7. The propagation material of claim 5, wherein the propagation material is suitable for vegetative reproduction, and is a cutting, a root, a stem, a cell or a protoplast.

8. The propagation material of claim 5, wherein the propagation material is suitable for tissue culture of regenerable cells and is a leaf, pollen, an embryo, a cotyledon, a hypocotyl, a meristematic cell, a root, a root tip, an anther, a flower, a seed, or a stem.

9. A method for identifying *Pythium* and *Didymella brioniae* resistance in a *Cucumis sativus* plant comprising using a marker comprising a sequence selected from SEQ ID NOS: 5-16 for screening a *Cucumis sativus* plant and selecting the *Cucumis sativus* plant having the marker, wherein presence of the marker identifies the plant as having *Pythium* and *Didymella brioniae* resistance.

10. A method for producing a *Pythium* and *Didymella brioniae* resistant *Cucumis sativus* plant comprising
introducing by introgression the copy number variant region defined in claim 1.

11. A method for selecting a *Pythium* and *Didymella brioniae* resistant *Cucumis sativus* plant, comprising
genetically determining the presence of the copy number variant region defined in claim 1, and
selecting a plant that comprises the copy number variant region as a *Pythium* and *Didymella brioniae* resistant plant.

12. A seed comprising the copy number variant region defined in claim 1.

13. A method for producing a *Cucumis sativus* plant which is resistant against *Pythium* and *Didymella brioniae*, said method comprising:
a) crossing a first plant of claim 1 with a second plant to obtain an F1 population;
b) optionally performing one or more rounds of selfing and/or crossing a plant from the F1 of step a) to obtain a further generation population;
c) selecting from the F1 population of step a) or the further generation population of step b) a plant that comprises the copy number variant region of claim 1, which plant is resistant against *Pythium* and *Didymella brioniae*.

14. The method of claim 13, wherein the plant obtained from step c) is crossed with another plant to obtain a *Pythium* resistant hybrid plant.

* * * * *